US008118794B2

(12) United States Patent
Weston

(10) Patent No.: US 8,118,794 B2
(45) Date of Patent: Feb. 21, 2012

(54) REDUCED PRESSURE TREATMENT SYSTEM

(75) Inventor: Richard Scott Weston, Encinitas, CA (US)

(73) Assignee: BlueSky Medical Group, Inc., Memphis, TN (US)

( * ) Notice: Subject to any disclaimer, the term of this patent is extended or adjusted under 35 U.S.C. 154(b) by 0 days.

(21) Appl. No.: 12/938,291

(22) Filed: Nov. 2, 2010

(65) Prior Publication Data
US 2011/0046585 A1 Feb. 24, 2011

Related U.S. Application Data

(63) Continuation of application No. 10/652,100, filed on Aug. 28, 2003, now Pat. No. 7,846,141.

(60) Provisional application No. 60/407,783, filed on Sep. 3, 2002, provisional application No. 60/430,827, filed on Dec. 4, 2002.

(51) Int. Cl.
*A61M 1/00* (2006.01)
(52) U.S. Cl. .................. 604/315; 604/313; 604/543
(58) Field of Classification Search .......... 604/313–316, 604/543
See application file for complete search history.

(56) References Cited

U.S. PATENT DOCUMENTS

| | | | |
|---|---|---|---|
| 1,480,562 A | 1/1924 | Mock | |
| 2,280,915 A | 4/1941 | Johnson | |
| 2,568,933 A | 9/1951 | Robbins | |
| 2,632,443 A | 3/1953 | Lesher | |
| 2,682,873 A | 7/1954 | Evans et al. | |
| 3,334,626 A | 8/1967 | Schimmel | |
| 3,367,332 A | 2/1968 | Groves | |
| 3,486,504 A | 12/1969 | Austin et al. | |
| 3,572,340 A | 3/1971 | Lloyd et al. | |
| 3,610,238 A | 10/1971 | Rich et al. | |
| 3,874,387 A | 4/1975 | Barbieri | |
| 3,993,080 A | 11/1976 | Loseff | |
| 4,112,947 A | 9/1978 | Nehring | |
| 4,136,696 A | 1/1979 | Nehring | |
| 4,184,510 A | 1/1980 | Murry et al. | |
| 4,212,296 A | 7/1980 | Schaar | |

(Continued)

FOREIGN PATENT DOCUMENTS

CA 2198243 A1 2/1996

(Continued)

OTHER PUBLICATIONS

U.S. Appl. No. 12/192,000, filed Aug. 14, 2008, Hartwell et al.

(Continued)

*Primary Examiner* — Lynne Anderson
(74) *Attorney, Agent, or Firm* — Knobbe, Martens, Olson & Bear LLP

(57) ABSTRACT

A wound treatment apparatus is provided for treating tissue damage, which comprises a fluid impermeable wound cover sealed over a site for purposes of applying a reduced pressure to the site. The apparatus also includes a cover with protrusions on its surface for purposes of monitoring pressure at the site. An absorbable matrix may be placed in the site of a wound to encourage tissue growth into the matrix. Temperature of the site may be monitored using a layer of temperature sensitive material and temperature sensors connected to an alarm and recording device. A vacuum pump supplies suction within the wound cover over the treatment site. A portable version of the wound treatment apparatus is also provided. Finally, a method for treating wounds using reduced pressure is provided.

93 Claims, 7 Drawing Sheets

U.S. PATENT DOCUMENTS

| | | | |
|---|---|---|---|
| 4,217,894 A | 8/1980 | Franetzki | |
| 4,219,019 A | 8/1980 | Coates | |
| 4,224,945 A | 9/1980 | Cohen | |
| 4,250,882 A | 2/1981 | Adair | |
| 4,316,466 A | 2/1982 | Babb | |
| 4,382,441 A | 5/1983 | Svedman | |
| 4,465,485 A | 8/1984 | Kashmer et al. | |
| 4,525,166 A | 6/1985 | Leclerc | |
| 4,534,356 A | 8/1985 | Papadakis | |
| 4,573,965 A | 3/1986 | Russo | |
| 4,655,766 A | 4/1987 | Theeuwes et al. | |
| 4,681,562 A * | 7/1987 | Beck et al. | 604/543 |
| 4,778,446 A | 10/1988 | Jensen | |
| 4,792,328 A | 12/1988 | Beck et al. | |
| 4,820,284 A | 4/1989 | Hauri | |
| 4,921,488 A | 5/1990 | Maitz et al. | |
| 4,936,834 A | 6/1990 | Beck et al. | |
| 4,950,483 A | 8/1990 | Ksander et al. | |
| 4,969,880 A | 11/1990 | Zamierowski | |
| 4,972,829 A | 11/1990 | Knerr | |
| 4,979,944 A | 12/1990 | Luzsicza | |
| 5,055,198 A | 10/1991 | Shettigar | |
| 5,056,510 A | 10/1991 | Gilman | |
| 5,073,172 A | 12/1991 | Fell | |
| 5,100,396 A | 3/1992 | Zamierowski | |
| 5,149,331 A | 9/1992 | Ferdman et al. | |
| 5,152,757 A * | 10/1992 | Eriksson | 604/305 |
| 5,167,613 A | 12/1992 | Karami et al. | |
| 5,176,663 A | 1/1993 | Svedman et al. | |
| 5,261,893 A | 11/1993 | Zamierowski | |
| 5,266,928 A | 11/1993 | Johnson | |
| 5,279,550 A | 1/1994 | Habib et al. | |
| 5,279,608 A | 1/1994 | Cherif Cheikh | |
| 5,328,614 A | 7/1994 | Matsumura | |
| 5,358,494 A | 10/1994 | Svedman | |
| 5,380,280 A | 1/1995 | Peterson | |
| 5,445,604 A | 8/1995 | Lang | |
| 5,489,280 A | 2/1996 | Russell | |
| 5,498,338 A | 3/1996 | Kruger et al. | |
| 5,527,293 A | 6/1996 | Zamierowski | |
| 5,549,584 A * | 8/1996 | Gross | 604/313 |
| 5,636,643 A | 6/1997 | Argenta et al. | |
| 5,643,189 A * | 7/1997 | Masini | 602/58 |
| 5,645,081 A | 7/1997 | Argenta et al. | |
| 5,759,570 A | 6/1998 | Arnold | |
| 5,785,688 A | 7/1998 | Joshi et al. | |
| 5,830,198 A | 11/1998 | Henniges et al. | |
| 5,830,496 A | 11/1998 | Freeman | |
| 5,833,646 A * | 11/1998 | Masini | 602/58 |
| 5,857,502 A | 1/1999 | Buchalter | |
| 5,868,933 A | 2/1999 | Patrick et al. | |
| 5,964,723 A | 10/1999 | Augustine | |
| 6,024,731 A | 2/2000 | Seddon et al. | |
| 6,071,247 A | 6/2000 | Kennedy | |
| 6,071,267 A | 6/2000 | Zamierowski | |
| 6,135,116 A | 10/2000 | Vogel et al. | |
| D434,150 S | 11/2000 | Turney et al. | |
| 6,142,982 A * | 11/2000 | Hunt et al. | 604/313 |
| 6,168,800 B1 | 1/2001 | Dobos et al. | |
| 6,174,306 B1 | 1/2001 | Fleischmann | |
| 6,176,307 B1 | 1/2001 | Danos et al. | |
| 6,225,523 B1 * | 5/2001 | Masini | 602/58 |
| 6,255,552 B1 | 7/2001 | Cummings et al. | |
| 6,261,283 B1 * | 7/2001 | Morgan et al. | 604/540 |
| 6,287,521 B1 | 9/2001 | Quay et al. | |
| 6,345,623 B1 | 2/2002 | Heaton et al. | |
| 6,398,767 B1 | 6/2002 | Fleischmann | |
| 6,458,109 B1 | 10/2002 | Henley et al. | |
| 6,465,708 B1 | 10/2002 | Augustine | |
| 6,471,685 B1 | 10/2002 | Johnson | |
| 6,471,982 B1 | 10/2002 | Lydon et al. | |
| 6,482,491 B1 | 11/2002 | Samuelsen et al. | |
| 6,491,684 B1 | 12/2002 | Joshi et al. | |
| 6,553,998 B2 | 4/2003 | Heaton et al. | |
| 6,599,262 B1 * | 7/2003 | Masini | 602/2 |
| 6,648,862 B2 | 11/2003 | Watson | |
| 6,951,553 B2 * | 10/2005 | Bubb et al. | 604/327 |
| 6,979,324 B2 * | 12/2005 | Bybordi et al. | 604/313 |
| 7,022,113 B2 * | 4/2006 | Lockwood et al. | 604/313 |
| 7,108,683 B2 * | 9/2006 | Zamierowski | 604/304 |
| 7,361,184 B2 | 4/2008 | Joshi | |
| 7,569,742 B2 | 8/2009 | Haggstrom et al. | |
| 7,615,036 B2 | 11/2009 | Joshi et al. | |
| 7,708,724 B2 | 5/2010 | Weston | |
| 7,779,625 B2 | 8/2010 | Joshi et al. | |
| 7,790,945 B1 | 9/2010 | Watson, Jr. | |
| 7,838,717 B2 | 11/2010 | Haggstrom et al. | |
| 7,846,141 B2 | 12/2010 | Weston | |
| 7,909,805 B2 | 3/2011 | Weston | |
| 7,964,766 B2 | 6/2011 | Blott et al. | |
| 2001/0029956 A1 | 10/2001 | Argenta et al. | |
| 2001/0034499 A1 | 10/2001 | Sessions et al. | |
| 2002/0065494 A1 * | 5/2002 | Lockwood et al. | 604/313 |
| 2002/0068913 A1 | 6/2002 | Fleischmann | |
| 2002/0115952 A1 | 8/2002 | Johnson et al. | |
| 2002/0120185 A1 | 8/2002 | Johnson | |
| 2002/0143286 A1 | 10/2002 | Turney | |
| 2002/0150720 A1 | 10/2002 | Howard et al. | |
| 2002/0161346 A1 | 10/2002 | Lockwood et al. | |
| 2002/0183702 A1 * | 12/2002 | Henley et al. | 604/305 |
| 2002/0198503 A1 | 12/2002 | Risk et al. | |
| 2002/0198504 A1 | 12/2002 | Risk et al. | |
| 2003/0014022 A1 | 1/2003 | Lockwood et al. | |
| 2003/0014025 A1 | 1/2003 | Allen et al. | |
| 2003/0021775 A1 | 1/2003 | Freeman | |
| 2003/0040687 A1 | 2/2003 | Boynton et al. | |
| 2003/0050594 A1 | 3/2003 | Zamierowski | |
| 2003/0108587 A1 | 6/2003 | Orgill et al. | |
| 2003/0144619 A1 | 7/2003 | Augustine | |
| 2005/0070835 A1 | 3/2005 | Joshi | |
| 2005/0261642 A1 | 11/2005 | Weston | |
| 2006/0029650 A1 | 2/2006 | Coffey | |
| 2007/0167926 A1 | 7/2007 | Blott et al. | |
| 2007/0265585 A1 | 11/2007 | Joshi et al. | |
| 2007/0265586 A1 | 11/2007 | Joshi et al. | |
| 2008/0183119 A1 | 7/2008 | Joshi | |
| 2008/0188820 A1 | 8/2008 | Joshi | |
| 2009/0131888 A1 | 5/2009 | Joshi | |
| 2009/0299251 A1 | 12/2009 | Buan | |
| 2009/0299306 A1 | 12/2009 | Buan | |
| 2010/0100063 A1 | 4/2010 | Joshi et al. | |
| 2010/0160879 A1 | 6/2010 | Weston | |
| 2010/0160880 A1 | 6/2010 | Weston | |
| 2010/0174251 A1 | 7/2010 | Weston | |
| 2010/0268198 A1 | 10/2010 | Buan et al. | |
| 2010/0298793 A1 | 11/2010 | Blott et al. | |
| 2011/0009838 A1 | 1/2011 | Greener | |
| 2011/0028918 A1 | 2/2011 | Hartwell | |
| 2011/0054421 A1 | 3/2011 | Hartwell | |
| 2011/0054423 A1 | 3/2011 | Blott et al. | |

FOREIGN PATENT DOCUMENTS

| | | |
|---|---|---|
| CA | 2367460 A1 | 10/2000 |
| CA | 2390513 A1 | 5/2001 |
| CA | 2121688 C | 7/2001 |
| CA | 2408305 A1 | 11/2001 |
| CA | 2458285 A1 | 3/2003 |
| CA | 2157772 C | 9/2003 |
| DE | 3935818 A1 | 5/1991 |
| DE | 40 12 232 A1 | 10/1991 |
| DE | 198 44 355 | 4/2000 |
| DE | 20 2005 019 670 U1 | 6/2006 |
| EP | 0020662 B1 | 7/1984 |
| EP | 0355186 A | 2/1990 |
| EP | 0777504 B1 | 10/1998 |
| EP | 0782421 B1 | 7/1999 |
| EP | 0708620 B1 | 5/2003 |
| EP | 1088569 B1 | 8/2003 |
| FR | 1 163 907 | 10/1958 |
| GB | 114754 | 4/1918 |
| GB | 641061 | 8/1950 |
| GB | 1 224 009 A | 3/1971 |
| GB | 1549756 A | 8/1979 |
| GB | 2195255 A | 4/1988 |
| GB | 2378392 A | 2/2003 |
| JP | 2003-165843 | 6/2003 |
| SU | 1251912 A1 | 8/1986 |

| | | |
|---|---|---|
| WO | WO 84/01904 | 5/1984 |
| WO | WO 90/11795 | 10/1990 |
| WO | WO 91/00718 | 1/1991 |
| WO | WO 92/20299 | 11/1992 |
| WO | WO 96/05873 | 2/1996 |
| WO | WO 00/07653 | 2/2000 |
| WO | WO 00/50143 A | 8/2000 |
| WO | WO 00/59424 | 10/2000 |
| WO | WO 00/61046 | 10/2000 |
| WO | WO 01/19430 | 3/2001 |
| WO | WO 01/34223 | 5/2001 |
| WO | WO 01/85248 | 11/2001 |
| WO | WO 02/083046 | 10/2002 |
| WO | WO 2005/051461 | 6/2005 |

OTHER PUBLICATIONS

U.S. Appl. No. 60/559,727, filed Apr. 5, 2004, Weston.
U.S. Appl. No. 60/573,655, filed May 21, 2004, Weston.
Achterberg et al., "Hydroactive dressings and serum proteins: an in vitro study," Journal of Wound Care, vol. 5, No. 2, Feb. 1996.
Argenta, Louis C., et al., "Vacuum-Assisted Closure: A New Method for Wound Control and Treatment; Clinical Experience", Ann Plas Surg 1997;38:563-577 (Dec. 10, 1996).
Aubrey, D.A., et al., Treatment of the Perineal Wound after Proctectomy by Intermittent Irrigation, Arch. Surg., Oct. 1984, 119, pp. 1141-1144.
Bagautdinov, N.A. "Variant of External Vacuum Aspiration in the Treatment of Purulent Diseases of Soft Tissues," in Current Problems in Modern Clinical Surgery: Interdepartmental Collection, edited by V.Ye. Volkov et al. (Chuvashia State University, Cheboksary, USSR 1986) pp. 94-96.
Biblehimer, Helen L., "Dealing With a Wound that Drains 1.5 Liters a Day," RN, Aug. 1986, pp. 21-23, USA.
Bier, A., Hyperemia as a Therapeutic Agent, Ed. Dr. Gustavus M. Blech, A. Robertson & Co., Chicago 1905, pp. 74-85.
Brubacher, "To Heal a Draining Wound", RN Mar. 1982, 7 pages.
Bucalo et al. "Inhibition of Cell Proliferation by Chronic Wound Fluid." Wound Repair and Regeneration, Miami, 1993, pp. 181-186.
Chariker, M.E., et al, Effective Management of Incisional and Cutaneous Fistulae with Closed Suction Wound Drainage, Contemporary Surgery. Jun. 1989, vol. 34 USA, pp. 59-63.
Costunchenok, BM, Effect of Vacuum on Surgical Purulent Wounds, Vestnik Chirurgia, 1986, 6 pages.
Davidov et al. "Pathogenic Mechanism of the Effect of Vacuum Therapy on the Course of the Wound Process" pp. 43-46 (Dec. 1990).
Davydov, Y., "Bacteriological and cytological evaluation of the vacuum therapy of suppurative wounds," Vestnik Khirurgii, Oct. 1988, pp. 48-52.
Davydov, Y., "Vacuum therapy in the treatment of purulent lactation mastitis," Vestnik Khirurgii, Sep. 1986, pp. 66-70.
Davydov, Yu A., et al., "Concepts for Clinical Biological Management of the Wound Process in the Treatment of Purulent Wounds Using Vacuum Therapy", The Kremlin Papers: Perspectives in Wound Care, Russian Journal: Vestnik Khirurgii, BlueSky Publishing, La Costa, California (2004), 15-17.
Davydov, Yu A., et al., "The Bacteriological and Cytological Assessment of Vacuum Therapy of Purulent Wounds", The Kremlin Papers: Perspectives in Wound Care, Russian Journal: Vestnik Khirurgii, BlueSky Publishing, La Costa, California (2004), 11-14.
De Lange, M.Y., et al., "Vacuum-Assisted Closure: Indications and Clinical Experience", Eur J Plast Surg (2000) 2;178-182 (Feb. 9, 2000).
Dilmaghani et al., A Method for Closed Irrigation and Suction Therapy in Deep Wound Infections, Journal of Bone and Joint Surgery, 1969, vol. 51-A, No. 2, pp. 323-342.
Fleischmann, Vacuum sealing: indication, technique, and results, European Journal of Orthopaedic Surgery & Traumatology (1995), pp. 37-40.
Fleischmann, W. Wund Forum Spezial. IHW '94. "Vakuumversiegelung zur Behandlung von Problemwuden" (with English translation: Vacuum Sealing for Treatment of Problematical Wounds).

Garcia-Rinaldi, R., et al., Improving the Efficiency of Wound Drainage Catheters, Amer. Journ. of Surg., Sep. 1975, pp. 130, 372-373.
Hartz, R.S., et al., Healing of the Perineal Wound, Arch. Surg., Apr. 1980, 115, pp. 471-474.
Jeter, K.F., et al, "Managing Draining Wounds and Fistulae: New and Established Methods", Chronic Wound Care, 1990, pp. 240-246.
Johnson, F.E., An Improved Technique for Skin Graft Placement using a Suction Drain, Surgery, Gynecology and Obstetrics, Dec. 1984, 3 pages.
Khirugii, Vestnik, "A Collection of Published Studies Complementing the Research and Innovation of Wound Care", The Kremlin Papers, Perspectives in Wound Care, Russian Medical Journal, Vestnik Khirugii, Blue Sky Publishing (2004), 2-17.
Kostiuchenok, B. M., et al., "The Vacuum Effect in the Surgical Treatment of Purulent Wounds", The Kremlin Papers: Perspectives in Wound Care, Russian Journal: Vestnik Khirurgii, BlueSky Publishing, La Costa, California (2004), 3-4.
Kremlin Papers, A Collection of Published Studies Complementing the Research and Innovation of Wound Care, from Vestnik Khirurgii, BlueSky Publishing, A Div. of BlueSky Medical Group Inc., 2004.
Landes, R.R. and I. Melnick, An Improved Suction Device for Draining Wounds, Arch. Surg., May 1972, 104, p. 707.
Linden, Willem van der, et al, "Randomized Trial of Drainage After Cholecystectomy: Suction Versus Static Drainage Through a Main Wound Versus a Stab Incision", American Journal of Surgery, Feb. 1981, vol. 141, pp. 289-294.
Mclaughlan, J, et al, "Sterile Microenvironment for Postoperative Wound Care", The Lancet, Sep. 2, 1978, pp. 503-504.
Meyer, W. and V. Schmeiden, Bier's Hyperemic Treatment, Published 1908 W. B. Saunders Company, pp. 44-65.
Morykwas, Michael J., et al., "Vacuum-Assisted Closure: A New Method for Wound Control and Treatment: Animal Studies and Basic Foundation", Ann Plast Surg 1997;38:553-562 (Dec. 10, 1996).
Nakayama, Y, et al, "A New Method for the Dressing of Free Skin Grafts", Plastic and Reconstructive Surgery, Dec. 1990 pp. 1216-1219, UK.
Office Action issued Jun. 9, 2011 for U.S. Appl. No. 12/848,817 in 25 pages.
Ramirez, O.M., et al., Optimal Wound Healing under Op-Site Dressing, Ideas and Innovations, 1983, 73(3), pp. 474-475.
Ranson, J. H. C., et al, "Safer Intraperitoneal Sump Drainage", Surgery, Gynecology & Obstetrics, Nov. 1973, vol. 137, pp. 841-842.
Sames, C.P., Sealing of Wounds with Vacuum Drainage, Br. Med. Journ., Nov. 5, 1977, p. 1223, Correspondence.
Solovev et al., "The Method of Treatment of Immature External Fistulas in the Upper Gastrointestinal Tract," USSR Ministry of Health, S.M. Kirov Gorky State Medical Institute, 1987.
Stewart, Joanne, "Next generation products for wound management," http://www.worldwidewounds.com/2003/april/Stewart/Next-Generation-Products.html, Nov. 2002.
Svedman, P., A Dressing Allowing Continuous Treatment of a Biosurface, IRCS Med. Science: Biomed. Tech.; Clinic. Med.; Surg. and Transplantation, 1979, 7, p. 221.
Svedman, P., et al., A Dressing System Providing Fluid Supply and Suction Drainage Used for Continuous or Intermittent irrigation, Annals of Plastic Surgery, vol. 17, No. 2, Aug. 1986, pp. 125-133.
Svedman, P., Irrigation Treatment in Split-Thickness Skin Grafting of Intractable Leg Ulcers, Scand J. Plast. Reconst. Surg., 1985, 19, pp. 211-213.
Svedman, P., Irrigation Treatment of Leg Ulcers, The Lancet, Sep. 1983, pp. 532-534.
Swift, et al, Quorum Sensing in *Aeromonas hydrophila and Aeromonas salmoncida*: Identification of LuxRI Homologs AhyRI and AsaRI and Their Cognate N-Acylhomoserine Lactone Signal Molecules, J. Bacteriol., 1997, 179(17):5271-5281.
Teder and Svedman et al., Continuous Wound Irrigation in the Pig, Journal of Investigative Surgery, 1990, vol. 3, pp. 399-407.
Tribble, David E. M.D., An Improved Sump Drain-Irrigation Device of Simple Construction, Archives of Surgery New York, 1972, vol. 105, pp. 511-513.
Usupov, Y. N., et al., "Active Wound Drainage", The Kremlin Papers: Perspectives in Wound Care, Russian Journal: Vestnik Khirurgii, BlueSky Publishing, La Costa, California (2004), 8-10.

Vijanto, J. and J. Raekallio, Local Hyperalimentation of Open Wounds, Br. J. surg., 1976, 63, pp. 427-430.

Westaby, S., et al., A Wound Irrigation Device, The Lancet, Sep. 2, 1978, pp. 503-504.

Wooding-Scott, Margaret, et al., No Wound is Too Big for Resourceful Nurses, RN, USA, Dec. 1988, pp. 22-25.

Wu, W.S., et al. Vacuum therapy as an intermediate phase in would closure: a clinical experience, Eur J Plast Surg (2000) 23: pp. 174-177.

* cited by examiner

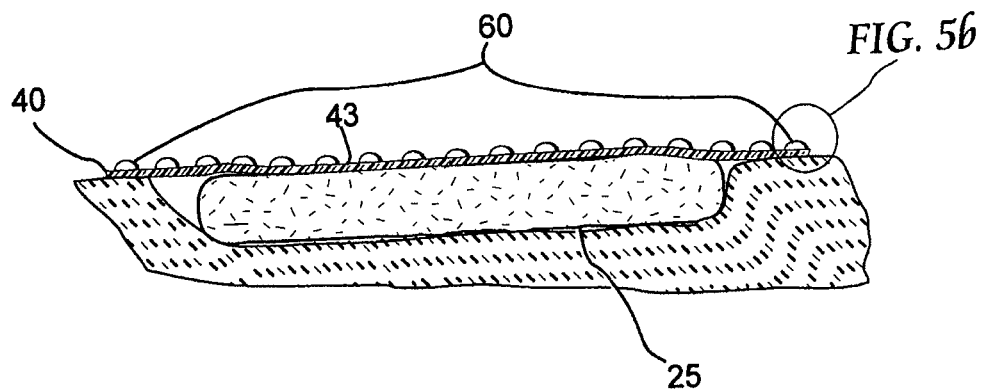
FIG. 5a
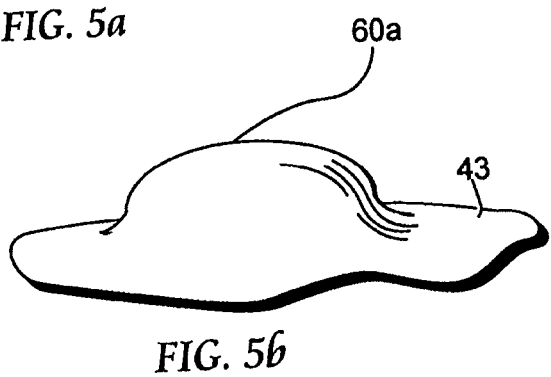
FIG. 5b
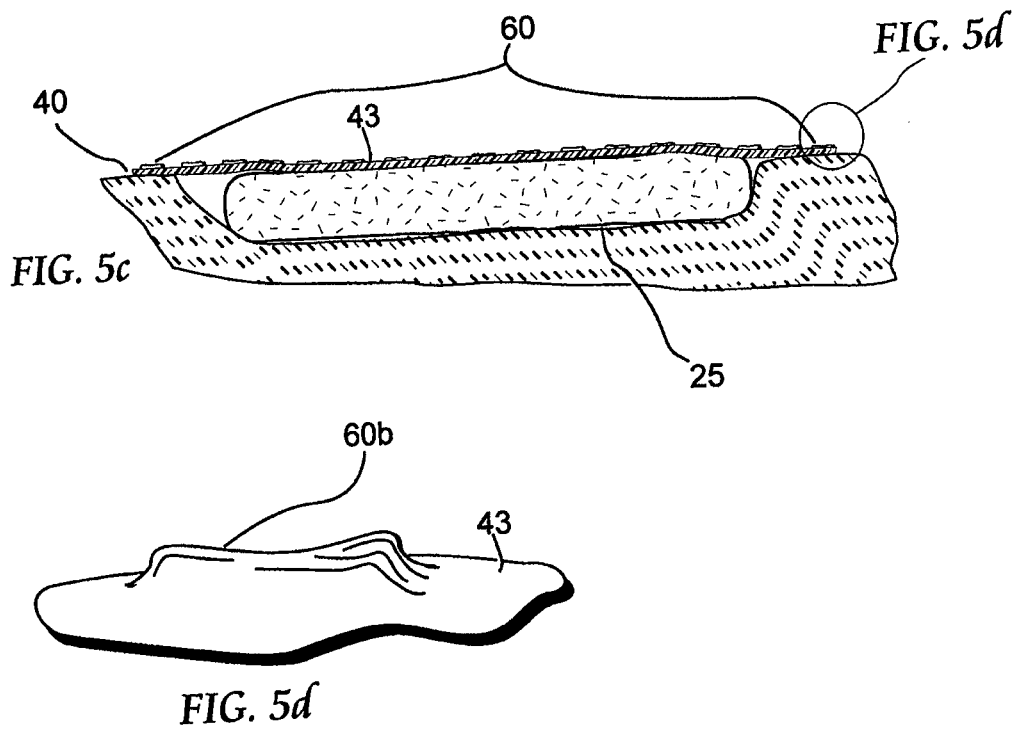
FIG. 5c
FIG. 5d

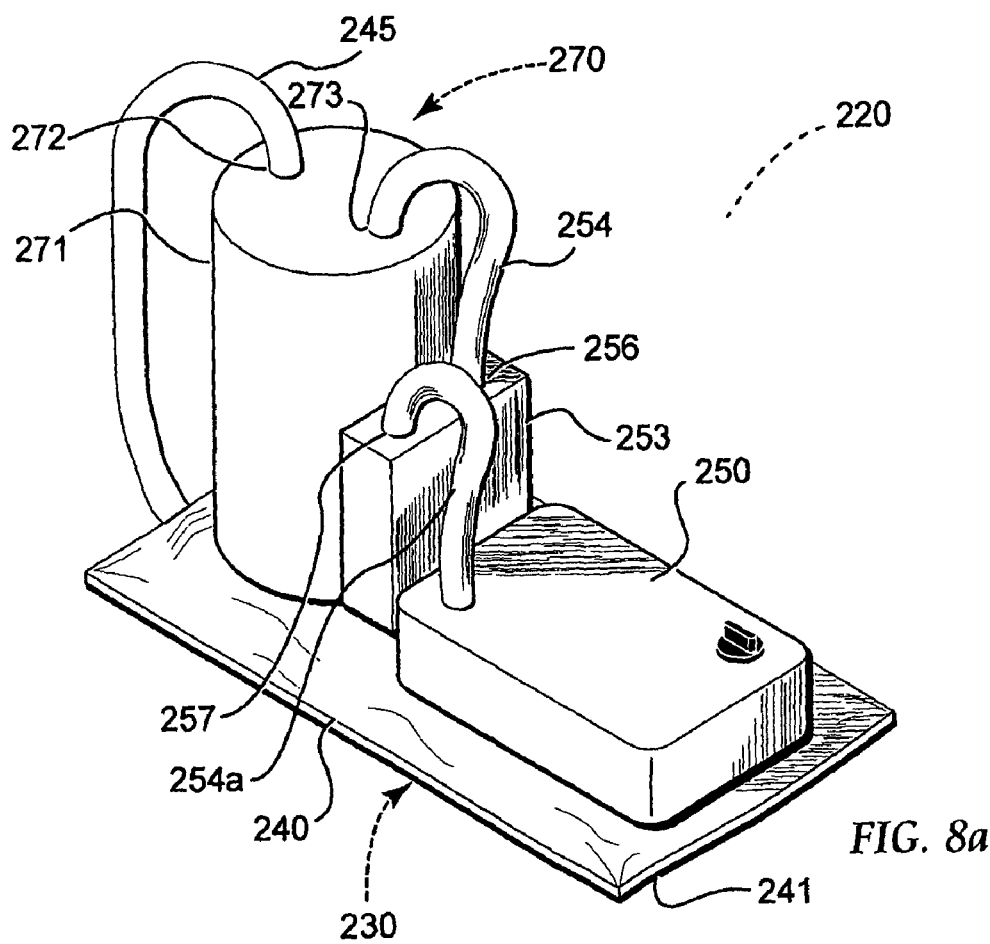
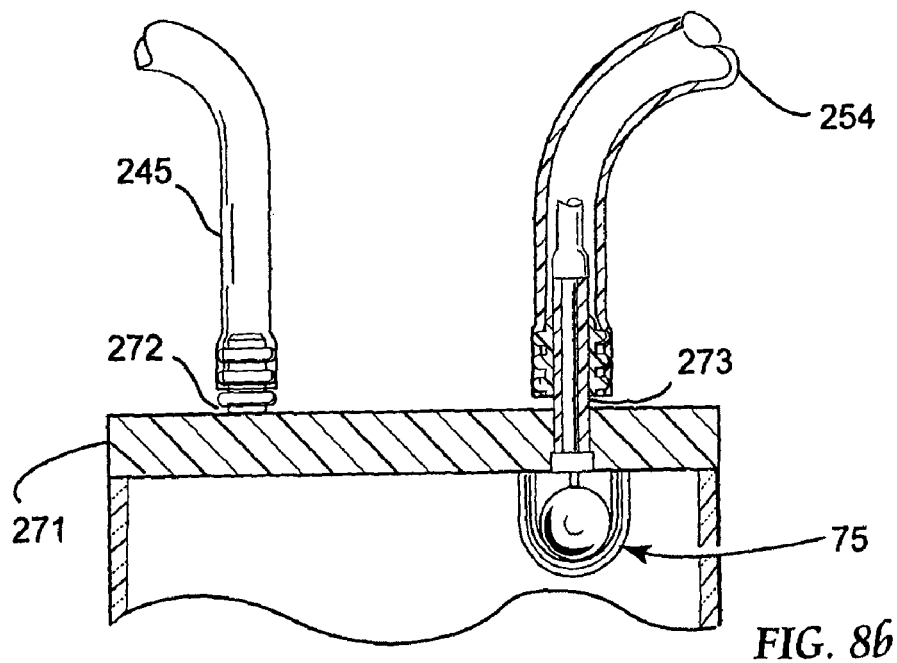

REDUCED PRESSURE TREATMENT SYSTEM

CROSS-REFERENCE TO RELATED APPLICATIONS

This application is a continuation application of U.S. patent application Ser. No. 10/652,100, filed on Aug. 28, 2003, and claims the benefit of U.S. Provisional Patent Application No. 60/407,783, filed on Sep. 3, 2002, and U.S. Provisional Patent Application No. 60/430,827, filed on Dec. 4, 2002, the entirety of all three of which are hereby incorporated by reference and made a part of the present disclosure as if fully set forth herein.

BACKGROUND OF THE INVENTION

1. Field of the Invention

The present invention relates to an apparatus and a method for treating a wound by applying reduced pressure to the wound. In this context, the term "wound" is to be interpreted broadly, to include any body part of a patient that may be treated using reduced pressure.

2. Description of the Related Art

The treatment of open or chronic wounds that are too large to spontaneously close or otherwise fail to heal has long been a troublesome area of medical practice. Closure of an open wound requires inward migration of surrounding epithelial and subcutaneous tissue. Some wounds, however, are sufficiently large or infected that they are unable to heal spontaneously. In such instances, a zone of stasis in which localized edema restricts the flow of blood to the epithelial and subcutaneous tissue forms near the surface of the wound. Without sufficient blood flow, the wound is unable to successfully fight bacterial infection and is accordingly unable to close spontaneously.

An initial stage of wound healing is characterized by the formation of granulation tissue which is a matrix of collagen, fibronectin, and hyaluronic acid carrying macrophages, fibroblasts, and neovasculature that forms the basis for subsequent epithelialization of the wound. Infection and poor vascularization hinder the formation of granulation tissue within wounded tissue, thereby inhibiting wound healing. It therefore becomes desirable to provide a technique for increasing blood circulation within wounded tissue to promote spontaneous healing and to reduce infection.

Another problem encountered during the treatment of wounds is the selection of an appropriate technique for wound closure during the healing process. Sutures are often used to apply force to adjacent viable tissue in order to induce the edges of a wound to migrate together and heal. However, sutures apply a closure force to only a very small percentage of the area surrounding a wound. When there is scarring, edema, or insufficient tissue, the tension produced by the sutures can become great causing excessive pressure to be exerted by the sutures upon the tissue adjacent to each suture. As a result, the adjacent tissue often becomes ischemic thereby rendering suturing of large wounds counterproductive. If the quantity or size of the sutures is increased to reduce the tension required of any single suture, the quantity of foreign material within the wound is concomitantly increased and the wound is more apt to become infected. Additionally, the size or type of a particular wound may prevent the use of sutures to promote wound closure. It therefore becomes desirable to provide an apparatus and method for closing a large wound that distributes a closure force evenly about the periphery of the wound.

Wounds resulting from ischemia, or lack of blood flow, are also often difficult to heal since decreased blood flow to a wound may inhibit normal immune reaction to fight infection. Patients that are bedridden or otherwise non-ambulatory are susceptible to such ischemic wounds as decubitus ulcers or pressure sores. Decubitus ulcers form as a result of constant compression of the skin surface and underlying tissue thus restricting circulation. Since the patient is often unable to feel the wound or to move sufficiently to relieve the pressure, such wounds can become self-perpetuating. Although it is common to treat such wounds with flaps, the conditions that initially caused the wound may also work against successful flap attachment. Wheelchair-bound paraplegics, for example, must still remain seated after treatment of pelvic pressure sores. It therefore becomes desirable to provide a treatment procedure for ischemic wounds that can be conducted in situ upon an immobile or partially mobile patient.

Other types of wounds in which ischemia leads to progressive deterioration include partial thickness burns. A partial thickness burn is a burn in which the cell death due to thermal trauma does not extend below the deepest epidermal structures such as hair follicles, sweat glands, or sebaceous glands. The progression of partial thickness burns to deeper burns is a major problem in burn therapy. The ability to control or diminish the depth of burns greatly enhances the prognosis for burn patients and decreases morbidity resulting from burns. Partial thickness burns are formed of a zone of coagulation, which encompasses tissue killed by thermal injury, and a zone of stasis. The zone of stasis is a layer of tissue immediately beneath the zone of coagulation. Cells within the zone of stasis are viable, but the blood flow is static because of collapse of vascular structures due to localized edema. Unless blood flow is re-established within the zone of stasis soon after injury, the tissue within the zone of stasis also dies. The death of tissue within the zone of stasis is caused by lack of oxygen and nutrients, reperfusion injury (re-establishment of blood flow after prolonged ischemia), and decreased migration of white blood cells to the zone resulting in bacterial proliferation. Again, it becomes desirable to provide a technique for treating burn wounds by enhancing blood circulation to the wounded tissue to inhibit burn penetration.

There exist various apparatus utilizing reduced pressure for treatment of these types of wounds. See, for example, U.S. Pat. No. 5,636,643. The apparatus existing in the art is generally comprised of a fluid impermeable cover that covers the wound, which is directly or indirectly connected to a source of suction so that an area of reduced pressure is created beneath the cover in the area of the wound. Some type of packing material, such as gauze, is also often placed in the area of the wound beneath the cover to prevent overgrowth of the wound. Apparatus existing in the relevant art, however, suffer from several disadvantages.

One such disadvantage is the necessity to change the packing material placed in the wound during the period of treatment. This requirement is expensive because multiple dressings are necessary and medical staff must expend time to change the dressings. In addition, there is an increased risk of infection and intrusion of other harmful foreign material into the wound area. It is therefore desirable to have a reduced pressure wound treatment system having a dressing that does not need to be changed, or needs to be changed fewer times, during the period of treatment.

In addition, the existing apparatus do not have adequate means to monitor the pressure in the area of the wound beneath the cover. If the cover is not adequately sealed to the tissue surrounding the wound, reduced pressure cannot be maintained beneath the cover so that the benefits of the treatment are lost or diminished. In addition, pressure leaks through the seal cause the source of suction to operate more frequently, which consumes more energy and causes the suction equipment to wear faster than it would otherwise, reducing its useful life. Further, the flow of air into the wound area as a result of such leaks can result in increased risk of infection and intrusion of other harmful foreign material into the wound area. It is therefore desirable to have a relatively inexpensive means of monitoring the pressure level beneath the cover at the site of the wound.

In addition, the existing apparatus do not have a means to determine the amount of blood flow to the tissue at the site of the wound. As discussed above, adequate blood circulation in the area of the wound is essential for the healing process to proceed as desired. Areas of tissue having an increased level of blood circulation generally have a higher temperature than areas that have a comparatively lower level of blood circulation. It is therefore desirable to have a means of monitoring the relative temperature within the area of the wound.

Finally, it is sometimes necessary to transport patients in need of reduced pressure wound care. It is also sometimes necessary to provide reduced pressure treatment in the field. It is therefore also desirable to have a wound treatment apparatus that is portable and self-contained, which can accompany the patient during such transport or be used to provide reduced pressure treatment in the field.

SUMMARY

The present invention is directed to a reduced pressure wound treatment apparatus and method that satisfy the needs described above. As described in greater detail below, it has many advantages over existing apparatus when used for its intended purpose, as well as novel features that result in a new reduced pressure wound treatment apparatus and method that are not anticipated, rendered obvious, suggested, or even implied by any of the prior art apparatuses, either alone or in any combination thereof.

In accordance with the present invention a wound treatment apparatus is provided for treating a wound by applying reduced pressure (i.e. pressure that is below ambient atmospheric pressure) to the wound in a controlled manner for a selected time period in a manner that overcomes the disadvantages of currently existing apparatus. The application of reduced pressure to a wound provides such benefits as faster healing, increased formation of granulation tissue, closure of chronic open wounds, reduction of bacterial density within wounds, inhibition of burn penetration, and enhancement of flap and graft attachment. Wounds that have exhibited positive response to treatment by the application of negative pressure include infected open wounds, decubitus ulcers, dehisced incisions, partial thickness burns, and various lesions to which flaps or grafts have been attached.

The wound treatment apparatus in accordance with the present invention includes a reduced pressure application appliance that is applied to a treatment site at which there is a wound and normal tissue surrounding the wound. The reduced pressure application appliance includes a fluid impermeable wound cover for covering and enclosing the wound. In a particular embodiment of the present invention, the wound cover also includes means for visually monitoring the pressure in the area of the site of the wound beneath the wound cover. These means include a plurality of protrusions on the surface of the cover that are recessed when a predetermined pressure is present beneath the cover, but are increasingly displaced above the remaining surface of the cover as the pressure beneath the cover increases above a predetermined pressure. In a similar manner, the cover may contain areas that are displaced as protrusions away from the remaining surface of the cover toward the wound when reduced pressure is applied beneath the cover, and the displacement of the protrusions decreases as the pressure beneath the cover increases. The protrusions may also be a different color (or a different shade of the same color) from that on the remaining surface of the cover. In addition, the protrusions may produce a noise as they are displaced away from the remaining surface of the cover, providing an audible indication that the pressure beneath the cover is increasing.

The appliance also includes sealing means for sealing the wound cover to the surrounding tissue of the wound in order to maintain reduced pressure in the vicinity of the wound during wound treatment. When the wound cover is sealed in position over the wound site, a generally fluid-tight or gas-tight sealed enclosure is formed over the wound site. The sealing means may be in the form of an adhesive applied to the underside of the wound cover for sealing the wound cover around the periphery of the wound. The sealing means may also include a separate sealing member such as an adhesive strip or a sealing ring in the form of a tubular pad or inflatable cuff secured to the wound cover for positioning around the periphery of the wound. In selected embodiments, the reduced pressure within the sealed enclosure under the wound cover may serve to seal the wound cover in position at the wound site. The reduced pressure appliance also includes a suction port for supplying reduced pressure within the sealed volume enclosed beneath the wound cover. The suction port may be in the form of a nipple on the wound cover. Alternatively, the suction port may be in the form of a tube attached to the wound cover or provided as a feedthrough beneath the wound cover.

The appliance may also include an absorbable matrix for placement in the wound in order to encourage tissue in the area of the wound to grow into the matrix during treatment. The absorbable matrix is constructed of an absorbable material that is absorbed into the epithelial and subcutaneous tissue in the wound as the wound heals. The matrix may vary in thickness and rigidity, and it may be desirable to use a spongy absorbable material for the patient's comfort if the patient must lie upon the appliance during treatment. The matrix may also be perforated and constructed in a sponge-type or foam-type structure to enhance gas flow and to reduce the weight of the matrix. Because of the absorbable nature of the absorbable matrix, the matrix should require less frequent changing than other dressing types during the treatment process. In other circumstances, the matrix may not need to be changed at all during the treatment process.

A vacuum system is connected with the reduced pressure appliance in order to provide suction or reduced pressure to the appliance. For this purpose, the vacuum system includes a suction pump or suction device for connection with the suction port of the appliance for producing the reduced pressure over the wound site. The vacuum system may include a section of hose or tube, such as a vacuum hose, that interconnects the suction device with the suction port of the appliance to provide the reduced pressure at the wound site. A fluid collection system may be provided intermediate the vacuum hose of the suction device and the suction port of the appliance to trap any exudate that may be aspirated from the wound by the negative pressure appliance. A stop mechanism may also be provided for the vacuum system to halt production of the reduced pressure at the wound site in the event that an excessive quantity of exudate has been collected. The apparatus may also include a control device for controlling the pump.

In a particular embodiment of the invention, the wound cover for the reduced pressure appliance may be in the form of a gas impermeable covering sheet of flexible polymer material, such as polyethylene, having an adhesive backing that provides the seal for securing the sheet over the wound site to provide a gas-tight or fluid-tight sealed enclosure over the wound site. The vacuum system of the wound treatment apparatus may include a suction pump having a vacuum hose that is connected with a suction tube serving as a suction port for the appliance. The suction tube for the appliance runs beneath the cover sheet that is sealed in position over the wound site and into the fluid-tight enclosure provided under the cover sheet. An adhesive backing on the cover sheet is used to provide a fluid-tight seal around the feedthrough for the suction tube at the wound site. Within the enclosure, the suction tube is connected with the absorbable matrix for placement in the wound. The absorbable matrix functions to more uniformly apply reduced pressure or suction over the wound site while holding the cover sheet substantially out of the wound during the application of reduced pressure at the enclosed wound site.

In another particular version of the invention, the wound treatment apparatus also includes means to monitor the temperature of the tissue in the area of the wound. In a particular embodiment of this version of the invention, a temperature sensitive layer composed of a temperature sensitive material is placed adjacent to the lower surface of the wound cover. The temperature sensitive layer changes color, or changes from one shade of a color to another shade of the same color, as the temperature of the material changes. In this embodiment of the invention, the wound cover is composed of a transparent or semi-transparent material allowing the temperature sensitive material to be observed from above the wound cover. Alternatively, the wound cover is composed of a temperature sensitive material that changes color, or changes from one shade of a color to another shade of the same color, as the temperature of the material changes. In another embodiment of this version of the invention, one or more temperature measuring devices are placed in the area of the wound. The temperature measuring devices are preferably placed adjacent to the wound tissue, but may also be placed in other locations under or above the wound cover, to monitor the temperature of said tissue. Temperature measuring devices located under the wound cover have leads that feedthrough beneath the wound cover. The leads are connected to an alarm system that produces one or more alarm signals when the temperature measured by one or more of the temperature measuring devices exceeds or is lower than a predetermined value. In another embodiment of this version of the invention, the temperature measuring devices are also connected through their respective leads and the alarm system to a temperature display or recording device that produces a display or record of the temperature in the area of the wound.

In another particular version of the invention, the wound treatment apparatus is portable and self-contained. In this version of the invention, a miniature vacuum source is used to provide suction to the reduced pressure appliance. Similarly, the fluid collection system is of the minimum size desired to collect and maintain the amount of exudate expected to be aspirated from the wound during the time of anticipated use of the portable wound treatment apparatus. A filter may also be placed in the connection between the vacuum source and the fluid collection system to avoid contamination of the source by the fluid aspirated from the wound. As a result, reduced pressure treatment of a wound can continue even if it becomes necessary to transport the patient because the apparatus can accompany a patient during the transport. The portable apparatus is not, however, limited to this use alone. It can be used in any application where a portable treatment apparatus is advantageous, such as treatment of wounds in the field.

There has thus been outlined, rather broadly, the more primary features of the present invention. There are additional features that are also included in the various embodiments of the invention that are described hereinafter and that form the subject matter of the claims appended hereto. In this respect, it is to be understood that the invention is not limited in its application to the details of construction and to the arrangements of the components set forth in the following description or illustrated in the following drawings. This invention may be embodied in the form illustrated in the accompanying drawings, but the drawings are illustrative only and changes may be made in the specific construction illustrated and described within the scope of the appended claims. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

The foregoing summary, as well as the following detailed description of the preferred embodiments of the present invention, will be better understood when read in conjunction with the appended drawings, in which:

FIG. 4b is a sectional elevational detailed view of the shutoff mechanism portion of the collection system of FIG. 4a;

FIG. 5a is a schematic sectional elevational view of a reduced pressure appliance in accordance with another embodiment of the present invention, shown in partial section, in which the reduced pressure appliance includes a flexible, fluid impermeable wound cover sealed over the wound, said cover having embedded within it protrusions that are displaced above the remaining surface of the cover;

FIG. 5b is a detailed perspective view of a protrusion from the reduced pressure appliance of FIG. 5a, in the fully displaced configuration;

FIG. 5c is a schematic sectional elevational view of the reduced pressure appliance of FIG. 5a, illustrating the cover having the protrusions in the depressed configuration when sufficient vacuum is present beneath the cover;

FIG. 5d is a detailed perspective view of a protrusion from the reduced pressure appliance of FIG. 5a, in the fully depressed configuration;

FIG. 8a is a perspective view of a wound treatment apparatus in accordance with another embodiment of the present invention, shown from above, in which a reduced pressure appliance, a vacuum source, a filter, and a fluid collection system are connected together as a compact and portable apparatus; and FIG. 8b is a sectional elevational detailed view of the shutoff mechanism portion of the collection system of FIG. 8a.

DETAILED DESCRIPTION OF THE PREFERRED EMBODIMENT

Figure 1:
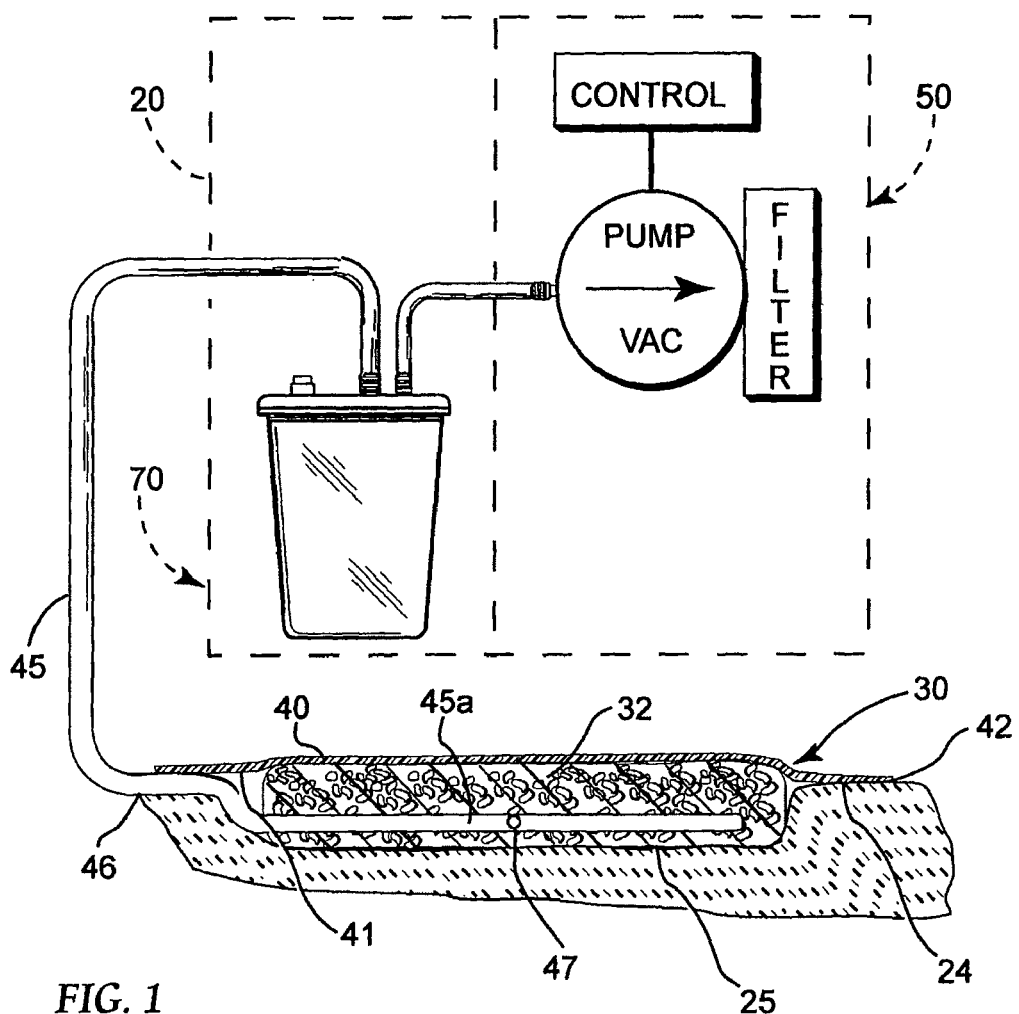
FIG. 1 is a schematic elevational view of a wound treatment apparatus in accordance with a particular embodiment of the present invention in which a reduced pressure appliance, shown in partial section, includes a flexible, fluid impermeable wound cover sealed over the wound and an absorbable matrix positioned in the wound, and in which a vacuum system provides reduced pressure within the wound cover of the appliance.

In accordance with the present invention, a wound treatment apparatus is provided for treating a wound by application of reduced pressure (i.e., below atmospheric pressure) so that suction may be applied to a wound site 25 in a controlled manner for a selected period of time. FIG. 1 schematically shows one version of the wound treatment apparatus, generally designated 20, which includes a reduced pressure appliance, generally designated 30, for enclosing a wound site 25 to provide a fluid-tight or gas-tight enclosure over the wound site 25 to effect treatment of a wound 25 with reduced or negative pressure. For the purpose of creating suction within the appliance 30, the appliance 30 is connected with a vacuum system, generally designated 50, to provide a source of suction or reduced pressure for the sealed appliance 30 at the wound site 25. Intermediate the appliance 30 and the vacuum system 50 is a fluid collection system, generally designated 70, for intercepting and retaining exudate that is aspirated from the wound site 25.

FIG. 1 also illustrates one embodiment of the reduced pressure appliance 30, which includes an absorbable matrix 32 that is placed within the wound 25, a fluid impermeable wound cover 40, and a suction port in the form of hollow tubing 45 that connects the appliance 30 to the vacuum system 50 (through the collection system 70) to provide reduced pressure in the area beneath the cover 40 in the area of the wound 25. FIG. 1 also illustrates one embodiment of an absorbable matrix 32, which is placed within the wound 25.

The absorbable matrix 32 is placed over substantially the expanse of the wound 25 to encourage growth of tissue in the area of the wound 25 into the matrix 32 as the wound heals. The size and configuration of the absorbable matrix 32 can be adjusted to fit the individual wound 25. It can be formed from a variety of absorbable materials, preferably a material that is also porous. The matrix 32 should be constructed in a manner so that it is sufficiently porous to allow oxygen to reach the wound 25. The absorbable matrix 32 is preferably constructed of a non-toxic material that is absorbable by the epithelial and subcutaneous tissue within the area of the wound 25, such as collogens derived from healthy mammals, absorbable synthetic polymers, or other materials similar to those used for absorbable dressings. An example is a dehydrating material derived from seaweed for treatment of exudating wounds. The matrix 32 may vary in thickness and rigidity, although it may be desirable to use a spongy or layered, non-woven absorbable material for the patient's comfort if the patient must lie upon the appliance 30 during treatment. The matrix 32 may also be perforated and constructed in a foam-type, sponge-type, or non-woven layered structure to enhance gas flow and to reduce the weight of the appliance 30. As shown in FIG. 1, the matrix 32 is cut to an appropriate shape and size to fit within the wound 25. Alternatively, the matrix 32 may be sufficiently large to overlap the surrounding skin 24. Further, the matrix 32 may be of uniform thickness over its entire area, as is the case where monitoring the temperature of tissue in the area of the wound is desired as a part of the treatment process.

Figure 2A:
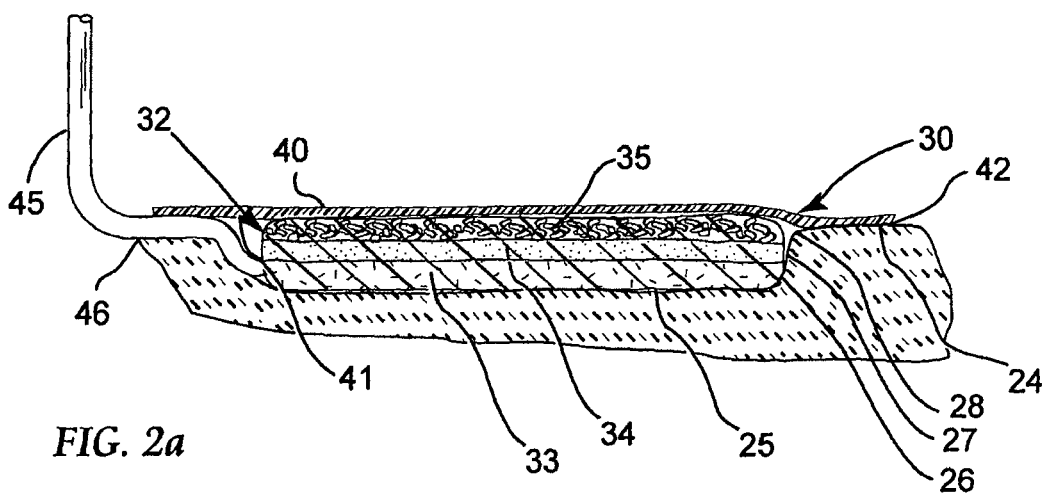
FIG. 2a is a schematic sectional elevational view of the reduced pressure appliance of FIG. 1, illustrating an absorbable matrix having three layers of absorbable material, such layers being of different absorbable materials.

In another embodiment of the invention, the absorbable matrix 32 has the same features as described above and as illustrated in FIG. 1, but may also be constructed of more than one absorbable material, such material having different rates of absorption into body tissue. By preselecting the materials of the matrix 32, and placing them in areas of the wound 25 in which different rates of absorption are desired, it may be possible to enhance wound healing. An example of this embodiment of the absorbable matrix 32 is illustrated in FIG. 2a, where the matrix 32 is composed of three layers, each layer being composed of an absorbable material different from the material in the adjacent layer. Thus, in a matrix 32 of three layers having the lowest layer 33 being constructed of an absorbable material, and the middle layer 34 of the matrix 32 being constructed of a material having a lower rate of absorption than the lowest layer 33, and the layer of the matrix 32 closest to the cover 40 (i.e., the highest layer 35) being constructed of a material having a rate of absorption lower than the other two layers, the area of the wound 25 adjacent to the lowest layer 26 would be allowed to close at a faster rate than the area of the wound 25 adjacent to the middle layer 27, and the area of the wound 25 adjacent to the highest layer 28 would be allowed to close at a faster rate than the area of the wound 25 adjacent to the middle layer 27 and the lowest layer 26. This embodiment of the invention is not limited to three layers or this gradation of absorption rates. Any combination of number of layers and absorbent materials desirable for wound treatment is possible and may be preferred. For example, the matrix 32 may have a highest layer 35 of absorbent material having a rate of absorption higher than the rate of absorption of the middle layer 34, which middle layer 34 has a higher rate of absorption than the rate of absorption of the lowest layer 33. Similarly, the highest layer 35 and the lowest layer 33 may have rates of absorption that are approximately equal to one another, such rate of absorption being greater or lesser than the rate of absorption of the middle layer 33.

Figure 2B:
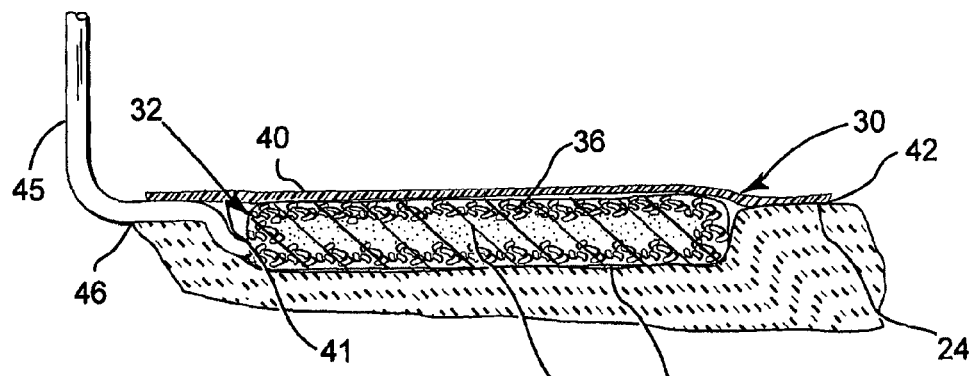
FIG. 2b is a schematic sectional elevational view of the reduced pressure appliance of FIG. 1, illustrating an absorbable matrix having generally concentric layers of absorbable material, such layers being of different absorbable materials.

In addition, this embodiment of the matrix 32 is not limited to layers. The matrix 32 may be constructed in any configuration having materials of different absorption rates in any portion of the matrix 32 that is desired to promote wound healing. For example, as illustrated in FIG. 2b, the material on the periphery 36 of the matrix 32 may be constructed of material having one rate of absorption, while the inner portions 37 of the matrix 32 may be constructed of one of more materials having different rates of absorption. This would allow for the wound 25 to close at one rate during the initial portion of the treatment period, and for the wound 25 to close at different rates during later portions of the treatment period. Other configurations that are possible include having approximately opposite sides or ends of the matrix 32 being constructed of a different material from the intermediate portions of the matrix 32.

The fluid-impermeable wound cover 40 in the embodiment of the reduced pressure appliance 30 illustrated in FIG. 1 is in the form of a flexible, adhesive, fluid impermeable polymer sheet for covering and enclosing the wound 25, including the absorbable matrix 32 within it, and the surrounding normal skin 24 at the wound site 25. The wound cover 40 includes an adhesive backing 41 which functions to seal the wound cover 40 to the normal skin 24 around the periphery of the wound 25 to provide a generally gas-tight or fluid-tight enclosure over the wound 25. The adhesive cover sheet 40 must have sufficient adhesion to form a fluid-tight or gas-tight seal 42 around the periphery of the wound 25 and to hold the sheet 40 in sealed contact with the skin 24 during the application of suction or reduced or negative pressure. The wound cover 40 also provides a gas-tight seal around the tubing 45 at the feedthrough location 46 where the tubing 45 emerges from beneath the wound cover 40. The wound cover 40 is preferably formed of a fluid impermeable or gas impermeable flexible adhesive sheet such as Ioban, a product of the 3M Corporation of Minneapolis, Minn.

Figure 3:
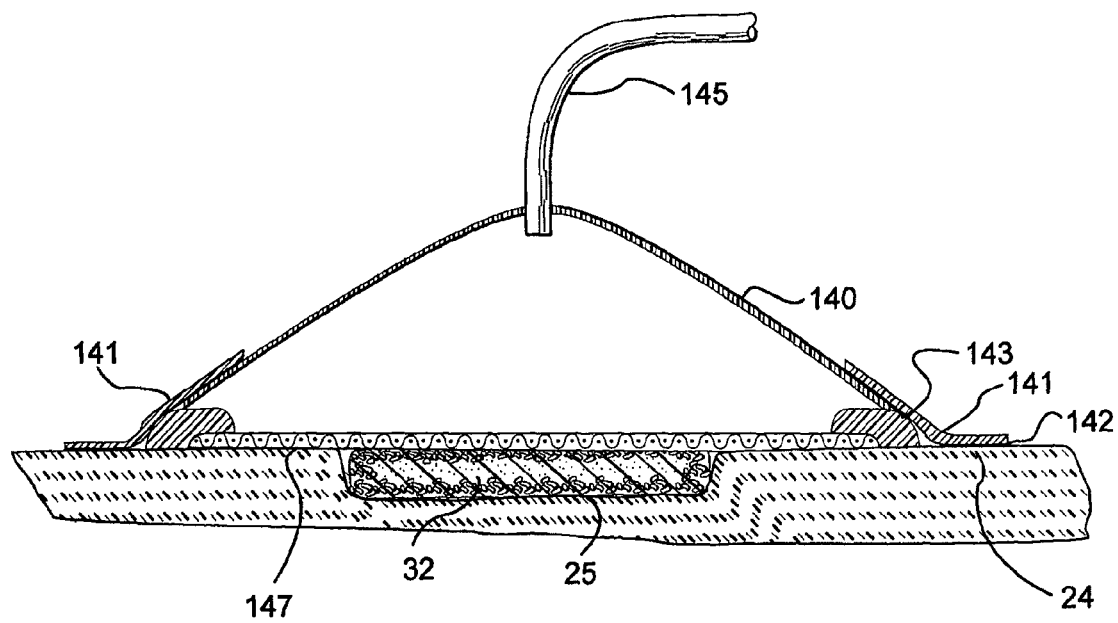
FIG. 3 is a schematic sectional elevational view of a reduced pressure appliance in accordance with another embodiment of the present invention, shown in partial section, in which the reduced pressure appliance includes a rigid, fluid impermeable, cone-shaped wound cover overlying the wound site.

The reduced pressure appliance 30 is not, however, limited to the configuration illustrated in FIG. 1. The appliance 30 may also have a wound cover of almost any size, shape, and configuration adapted to treat the wound. An example of this type of cover 40 is illustrated in the embodiment of the appliance 30 shown in FIG. 3, which has a wound cover 140 comprised of a rigid, fluid impermeable, generally cone-shaped wound cover 140 overlying the wound site 25. Alternatively, the cover overlying the wound site may be comprised of a rigid, fluid impermeable, flat, bowl-shaped, or cup-shaped wound cover to protect the site of a wound 25 from impact or abrasion during treatment. The wound cover may also be comprised of a fluid impermeable, flexible cover supported by rigid support members overlying the wound site 25. All of these cover types may be sealed to the normal skin 24 surrounding the wound 25 by using the suction created under the cover and a soft and flexible padding material 143 around the periphery of the cover 140, which is in contact with the skin 24. More preferably, the cover 140 is sealed to the skin 24 using a fluid-impermeable adhesive material 141 such as an adhesive tape or an adhesive sheet that has been cut to surround and at least partially overlie the periphery of the cover 140. As an additional example, the cover may be comprised of a CPR mask, which may be sealed to the skin surrounding the wound with an inflatable air cuff that is a part of the mask, with a fluid-impermeable adhesive material, or by some other fluid-impermeable means. Where the cover 140 is not in contact with the absorbable matrix 32, and is therefore not exerting force adequate to keep the matrix 32 in place within the wound 25, a rigid or semi-rigid porous screen 147 may be placed over the matrix 32 and under the cover 140 in a position so that the periphery of such screen 147 is held in place by a portion of the cover 140 or the seal 142 that holds the cover 140 in place against the skin 24. In such case, the screen 147 is of a thickness and rigidity necessary to hold the matrix 32 in place within the wound 25, but having a porous structure so that fluids (including gases) are able to pass through the screen 147.

The appliance 30 also includes a suction port in the form of a hollow suction tube 45 that connects with the vacuum system 50 to provide suction within the sealed enclosure. The suction tubing 45 serves as a suction port for the appliance 30. In the embodiment of the invention illustrated in FIG. 1, an end segment 45a of the tubing 45 is embedded within the absorbable matrix 32 for providing suction or reduced pressure within the enclosure provided under the wound cover 40. Embedding the open end of segment 45a of tubing 45 within the interior of the absorbable matrix 32 permits the absorbable matrix 32 to function as a shield to help prevent the wound cover 40 from being inadvertently sucked into sealing engagement with the open end of the tube thereby plugging the tube 45 and restricting gas flow. The tube segment 45a embedded within the absorbable matrix 32 preferably has at least one side port 47 for positioning within the interior of the absorbable matrix 32 to promote substantially uniform application of reduced pressure throughout the enclosure. Positioning the side port 47 of tube segment 45a within the interior of the absorbable matrix 32 permits the absorbable matrix 32 to function as a shield for the side port to thereby prevent the wound cover 40 from being sucked into the side port 47 and thereby restricting gas flow. The open cells of the absorbable matrix 32 facilitate gas flow throughout the enclosure. In addition, the absorbable matrix 32 functions to encourage the growth of tissue in the area of the wound 25 into the matrix 32 and to hold the wound cover 40 generally out of contact with the wound 25 during the application of suction within the enclosure.

Tubing 45 and tube segment 45a are sufficiently flexible to permit movement of the tubing but are sufficiently rigid to resist constriction when reduced pressure is supplied to the appliance 30 or when the location of the wound 25 is such that the patient must sit or lie upon the tubing 45 or upon the reduced pressure appliance 30. The matrix-tube assembly comprising the absorbable matrix 32 and the tube 45 may be fabricated by snaking the end of the tube segment 45a through an internal passageway in the absorbable matrix 32 such as by pulling the end of the tube segment 45a through the passageway using forceps. The matrix-tube assembly 32 and 45 is preferably prepared prior to use under sterile conditions and then stored in an aseptic package.

Figure 4A:
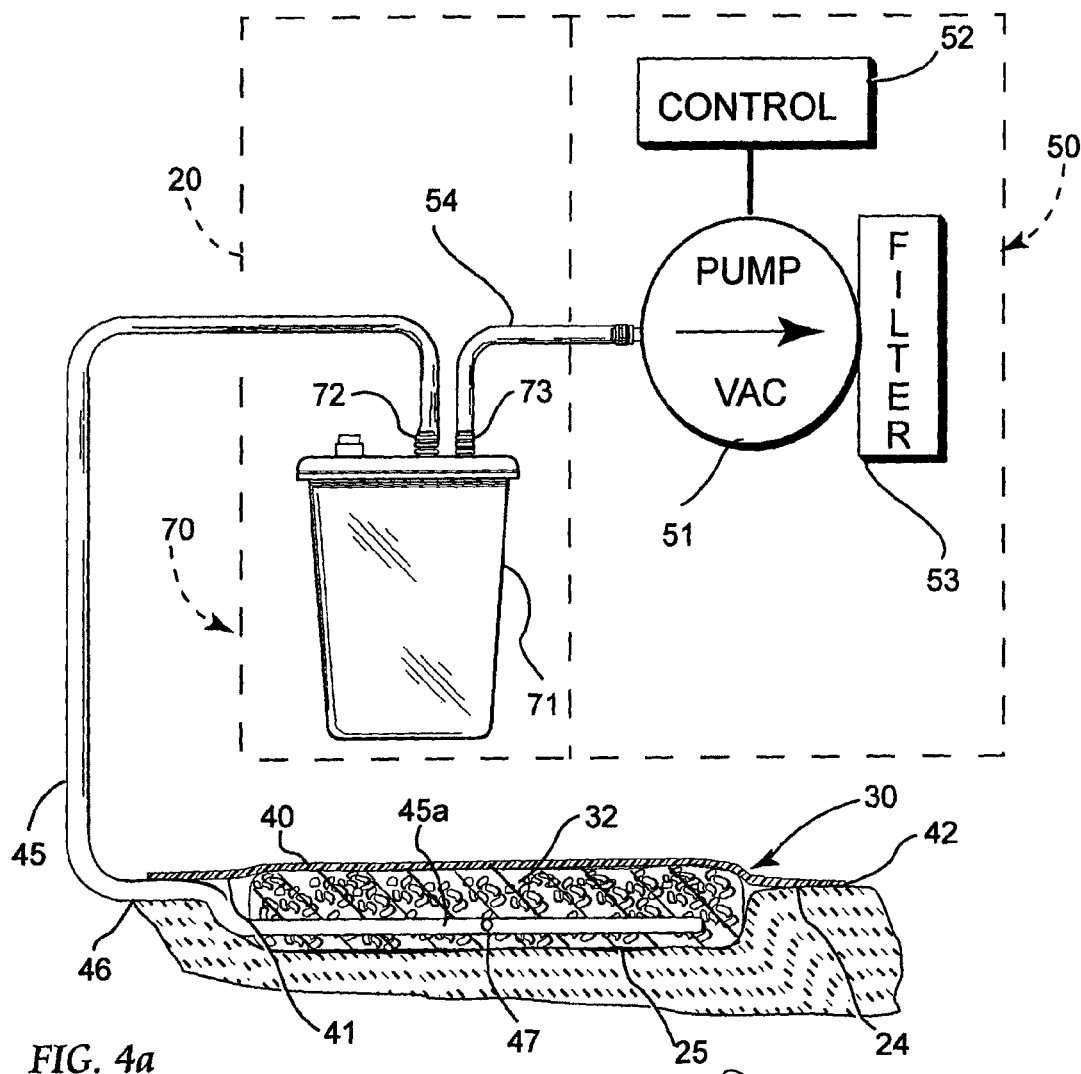
FIG. 4a is a schematic elevational view of a wound treatment apparatus in accordance with a particular embodiment of the present invention in which a reduced pressure appliance, shown in partial section, includes a flexible, fluid impermeable wound cover sealed over the wound and an absorbable matrix positioned in the wound, and in which a vacuum system provides reduced pressure within the wound cover of the appliance.

As shown in FIG. 4a, the vacuum system 50, which produces a source of reduced pressure or suction that is supplied to the reduced pressure appliance 30, includes a vacuum pump 51, a control device 52, a filter 53, and tubing 54 that connects the vacuum pump 51 to the collection system 70. Predetermined amounts of suction or reduced pressure are produced by the vacuum pump 51. The vacuum pump 51 is preferably controlled by a control device 52 such as a switch or a timer that may be set to provide cyclic on/off operation of the vacuum pump 51 according to user-selected intervals.

Alternatively, the vacuum pump 51 may be operated continuously without the use of a cyclical timer. A filter 53 such as micropore filter is preferably attached to the exhaust of the pump 51 to prevent potentially pathogenic microbes or aerosols from being vented to atmosphere by the vacuum pump 51.

As shown in FIG. 4*a*, a fluid collection system, generally designated 70, is interconnected between the suction pump 51 and the appliance 30 to remove and collect any exudate which may be aspirated from the wound 25 by the reduced pressure appliance 30. The appliance 30 functions to actively draw fluid or exudate from the wound 25. Collection of exudate in a fluid collection system 70 intermediate the pump 51 and the appliance 30 is desirable to prevent clogging of the pump 51. The fluid collection system 70 is comprised of a fluid-impermeable collection container 71 and a shutoff mechanism 75. The container 71 may be of any size and shape capable of intercepting and retaining a predetermined amount of exudate. Many examples of such containers are available in the relevant art. The preferred container in this embodiment of the invention is illustrated in side elevation view in FIG. 4*a*, said container having two openings in the top of the container 71. The container 71 includes a first port 72 at the top opening of the container for sealed connection to suction tubing 45. The first port 72 enables suction to be applied to the reduced pressure appliance 30 through the tubing 45 and also enables exudate from the wound 25 covered by reduced pressure appliance 30 to be drained into the container 71. The container 71 provides a means for containing and temporarily storing the collected exudate. A second port 73 is also provided on the top of the container to enable the application of suction from the vacuum pump 51. The second port 73 of the collection system 70 is connected to the vacuum pump 51 by a vacuum line 54. The collection system 70 is sealed generally gas-tight to enable the suction pump 51 to supply suction to the appliance 30 through the collection system 70.

The container 71 may also include a fluid impenetrable flexible liner within its volume that is used to collect the exudate in a manner that avoids contaminating the container 71 with pathogenic microbes and other harmful matter present in the exudate. In such case, the flexible liner may be directly connected to the first port 72 and second port 73 in a manner so that no exudate comes into direct contact with the container 71. In this embodiment, the preferred liner is a flexible bag constructed of a polymer material, which is connected to the first port 72.

The vacuum system 50 and collection system 70 preferably include a shutoff mechanism for halting or inhibiting the supply of the reduced pressure to the appliance 30 in the event that the exudate aspirated from the wound 25 exceeds a predetermined quantity. Interrupting the application of suction to the appliance 30 is desirable to prevent exsanguination in the unlikely event a blood vessel ruptures under the wound cover 40 during treatment. If, for example, a blood vessel ruptures in the vicinity of the wound 25, a shut-off mechanism would be useful to prevent the vacuum system 50 from aspirating any significant quantity of blood from the patient.

Figure 4B:
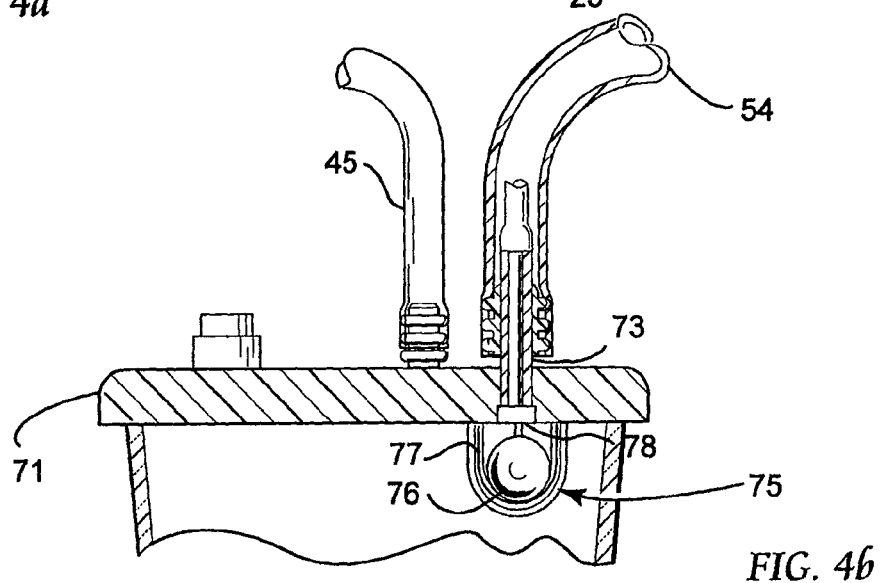

The shutoff mechanism 75 may be comprised of any means that enables the vacuum system 50 to halt the supply of reduced pressure to the wound cover 40 at any time that the volume of exudate from the wound 25 exceeds a predetermined amount. Such means may include mechanical switches, electrical switches operably connected to the vacuum system controller 52, optical, thermal or weight sensors operably connected to the vacuum system controller 52, and any other means that are currently known in the relevant art or which may hereafter be discovered. The shutoff mechanism 75, as illustrated in FIG. 4*b*, is preferably a float valve assembly in the form of a ball 76 which is held and suspended within a cage 77 positioned below a valve seat 78 disposed within the opening at the top of the container below the second port that will float upon the exudate and will be lifted against the valve seat 78 as the container fills with exudate. When the ball 76 is firmly seated against the valve seat 78, the float valve blocks the second port 73 and thereby shuts off the source of suction from the vacuum system 50. Other types of mechanisms may also be employed to detect the liquid level within the container 71 in order to arrest operation of the vacuum system 50.

Figure 5E:
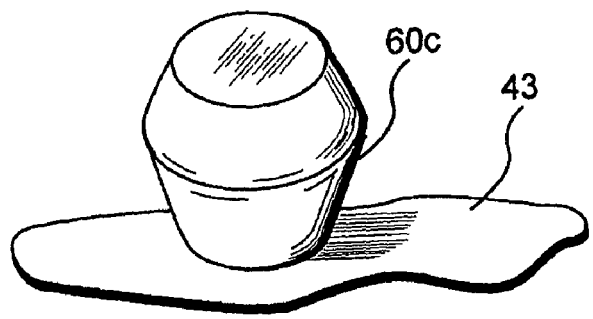
FIG. 5e is a schematic sectional elevational view of the reduced pressure appliance of FIG. 5a, illustrating alternative protrusions having a bellows-type of configuration.
Figure 5F:
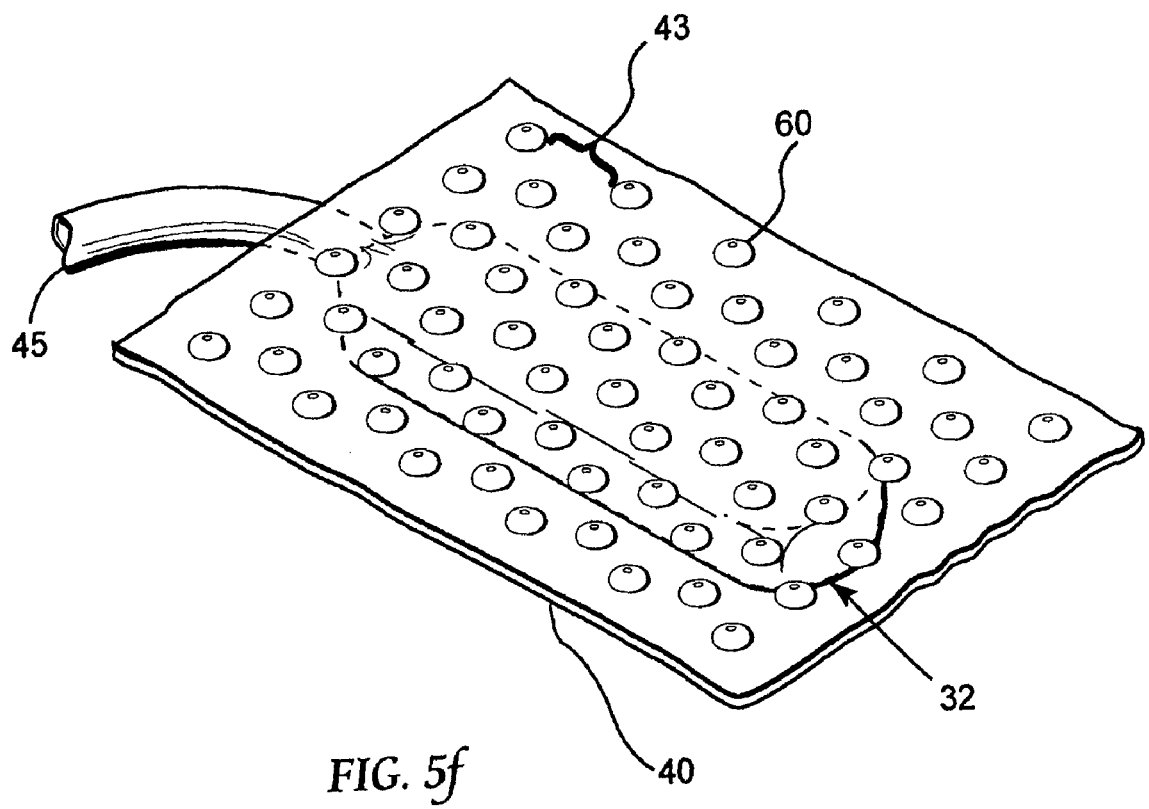
FIG. 5f is a perspective view of the reduced pressure appliance of FIG. 5a, illustrating a pattern of protrusions on the wound cover.

In another version of the invention, the wound treatment apparatus includes means to monitor the pressure beneath the wound cover 40 at the site of the wound 25. In one embodiment of this version of the invention, as illustrated in FIG. 5*a*, the wound cover 40 has a plurality of protrusions 60 in the form of hills or bumps embedded in the cover 40. As illustrated in FIG. 5*a*, the protrusions 60 protrude above the remaining surface 43 of the cover 40 when the cover 40 is not in use for wound treatment. A detailed view of a protrusion 60*a* in this configuration is shown in perspective view in FIG. 5*b*. Generally, as illustrated in FIG. 5*c*, in some embodiments, when the cover 40 is in use (i.e., sealed over the wound site 25 with reduced pressure applied beneath the cover 40), the protrusions 60 are displaced inwardly (or downward when the cover 40 is in the orientation depicted in FIG. 5*c*) so that they are depressed to a level almost the same as that of the remaining surface 43 of the cover 40. A detailed view of a protrusion 60*b* in the depressed configuration is shown in perspective view in FIG. 5*d*. In another embodiment, the protrusions 60*c* are configured in the form of bellows, as shown in FIG. 5*e*. In this version of the invention, as the pressure beneath the cover 40 decreases (i.e., the level of reduced pressure increases), the top of the protrusion 60*c* is displaced downward toward the level of the remaining surface 43 of the cover 40. The protrusions 60 may be placed in any location, as well as in any pattern or lack of pattern, on the surface of the cover 40. An example of one possible pattern is illustrated in FIG. 5*f*.

The protrusions 60 may be constructed of the same material as the remainder of the cover 40, or may be constructed of a material different from the remainder of the cover 40, depending upon the sensitivity of pressure monitoring desired. Similarly, the protrusions 60 may be constructed of material having the same thickness as the remainder of the cover 40, or material of a different thickness, depending upon the sensitivity of pressure monitoring desired. For example, if the reduced pressure beneath the cover 40 is of a relatively low level, so that the difference between the ambient atmospheric pressure above the cover 40 is relatively small when compared to the reduced pressure beneath the cover 40, it may be desirable to have the protrusions 60 be able to change shape with relatively small changes in pressure beneath the cover 40 during the treatment period. In such case, it may be preferable to have the protrusions 60 of a thickness less than the thickness of the remaining cover material. It may also be preferable to have the protrusions 60 constructed of a material more pliable than the material of which the remainder of the cover 40 is constructed. Similarly, if the reduced pressure beneath the cover 40 is of a relatively high level, so that the difference between the ambient atmospheric pressure above the cover 40 is relatively large when compared to the reduced pressure beneath the cover 40, it may be desirable to have the protrusions 60 be able to change shape with relatively large changes in pressure beneath the cover 40 during the treatment period. In such case, it may be preferable to have the protrusions 60 of a thickness more similar to the thickness of the remaining cover material. It may also be preferable to have the protrusions 60 constructed of a material that is more similar to the material of which the remainder of the cover 40 is constructed in terms of pliability.

By preselecting the thickness and pliability of the material used to construct the protrusions 60, it may also be possible to monitor the pressure by partial deflections of the protrusions 60. For example, the protrusions 60 may be displaced in an increasing amount above the remaining surface 43 of the cover 40 as the pressure beneath the cover 40 increases (i.e., the level of reduced pressure decreases). This relationship of displacement of the protrusions 60 to the increase in pressure beneath the cover 40 may be linear or based upon some other function. Similarly, the protrusions 60 may be constructed so that they only begin to be displaced when a predetermined pressure differential occurs between the area under the cover 40 and the area above the cover 40. It should be noted, however, that this version of the invention is intended as a means to provide an inexpensive and approximate visual indication of the occurrence of loss of reduced pressure beneath the cover and may not be a means to accurately measure the actual pressure beneath the cover or the actual difference between the pressure above the cover and the reduced pressure beneath the cover.

As a result, the preferable thicknesses and materials to be used in constructing the cover 40 and protrusions 60 in this version of the invention are dependent upon a multitude of factors, including the desired pressure beneath the cover 40. Preferably, the wound cover 40 is constructed of polyurethane, having a thickness of only a few mils to $\frac{1}{8}$th inch, and having protrusions 60 constructed of the same material as the remaining portion of the cover 40, said protrusions 60 having a thickness only slightly less than the thickness of the cover 40 to a relatively small fraction of the thickness of the cover 40.

Further, the protrusions 60 may be constructed of material that is of a different color than the color of the remaining surface 43 of the cover 40. Similarly, the protrusions 60 may be of a different shade of the same color as the remaining surface 43 of the cover 40. As the protrusions 60 are displaced away from the remaining surface 43 of the cover 40, the protrusions 60 may change color as a result of the expansion of the material comprising the protrusions 60.

In another embodiment of this version of the invention, the protrusions work in the manner opposite to that described above. In this embodiment, the cover has within it a plurality of areas that are displaced away (i.e., pulled down) from the remaining surface of the cover toward the wound when reduced pressure is applied beneath the cover. This downward displacement is the result of the reduced pressure suction, which causes tension that pulls the protrusions away from the remaining surface of the cover. As the pressure beneath the cover increases, the tension on the protrusions weakens allowing the protrusions to recede back into the cover. The principles discussed above with respect to thickness, materials, color, and partial deflection monitoring of pressure apply to this embodiment of the invention as well. It should be noted that bellows-type protrusions are not used in this embodiment.

The protrusions 60 may also have a means whereby they produce an audible sound as the protrusions 60 are being displaced away from the remaining surface 43 of the cover 40. This sound may be produced by the "crinkling" or vibration of the material as it is displaced away from the remaining surface 43 of the cover 40.

It should be noted that the means to monitor the pressure beneath the cover described in this embodiment of the invention may be used independently of any other feature of this invention. In addition, the means to monitor pressure beneath the cover is not limited to use in treatment of open wounds, decubitus ulcers, dehisced incisions, partial thickness burns, and various lesions to which flaps or grafts have been attached. Instead, said pressure monitoring means may be used in any application involving reduced pressure in the treatment of any portion of the body of a patient, such as cosmetic surgery, cosmetic healing, and prophylactic suctioning for cosmetic and psychological reasons. In addition, the cover may be of any configuration, including the cover configurations specifically discussed above. Further, it is not necessary that any packing material or matrix be present in the area of the wound beneath the cover in this version of the invention. Nor is it necessary that the features included in this version of the invention be included as a part of any other version or embodiment of this invention.

Figure 6:
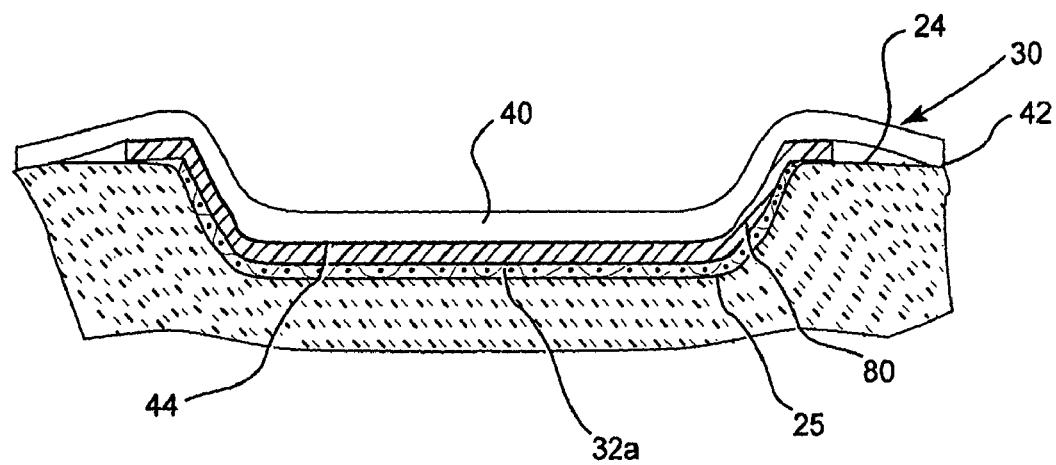
FIG. 6 is a schematic sectional elevational view of a reduced pressure appliance in accordance with another embodiment of the present invention, shown in partial section, in which the reduced pressure appliance includes a packing material or an absorbable matrix positioned in the wound, and a flexible, fluid impermeable wound cover sealed over the wound, and a layer of temperature sensitive material located between the cover and the wound.

In another version of the invention, the wound treatment apparatus includes means to monitor the temperature in the area of the wound 25. In one embodiment of this second version of the invention, as illustrated in FIG. 6, a layer of temperature sensitive material 80 is placed adjacent to the lower surface 44 of the wound cover 40. Alternatively, the cover 40 and the layer 80 may be joined together to form a single integrated unit. In such case, the cover 40 and the layer 80 may be joined in any manner that is fluid-impermeable and allows the color (or other property exhibiting the change of temperature) of the temperature sensitive layer 80 to be observed from above the wound cover 40. The preferred means to join the cover 40 and the layer 80 is a transparent or semi-transparent adhesive material. Alternatively, the wound cover 40 may itself be composed of a temperature sensitive material, so that a separate temperature sensitive layer is not required.

The temperature sensitive layer 80 (or the cover 40, if it is composed of a temperature sensitive material) may be composed of any material that changes properties in a manner that does not adversely affect the operation of the reduced pressure appliance 30. Preferably, the temperature sensitive layer 80 is composed of a material that changes color, or changes from one shade of a color to another shade of the same color, as the temperature of the material changes. The change in color or shade preferably occurs within the temperature range that may be expected in the area of the wound 25. In other words, the change in color or shade of the material should be significant enough to adequately indicate changes in temperature within the range of temperatures expected in the area of the wound 25. More preferably, the temperature sensitive material is a material that changes color in the range from approximately 95 degrees Fahrenheit to approximately 105 degrees Fahrenheit.

In the embodiment of the invention shown in FIG. 6, the temperature sensitive layer 80 is placed over a packing material or matrix 32a, which packing material or matrix 32a is placed within the area of the wound 25. The matrix 32a may be an absorbable matrix 32a, as described above. The packing material may be constructed of any material that is suitable for placement within a wound 25, which may be to prevent its overgrowth, but still allows for fluid and gas flow to and from the wound 25, such as a porous polymer material or gauze. In order to provide for uniform temperature monitoring, the packing material or matrix 32a is preferably of relatively uniform thickness when placed within the area of the wound 25. In addition, the packing material or matrix 32a should be thin enough to allow for the temperature of the tissue to affect the temperature of the temperature sensitive layer 80. More preferably, the thickness of the packing material or matrix 32a should not exceed slightly greater than zero to one half inches. The packing material or matrix 32a may, however, be of non-uniform thickness where the temperature sensitive layer 80 is comprised of temperature sensitive material in a manner that compensates for the differences in thickness of the packing material or matrix 32a.

The wound cover 40 is placed over the temperature sensitive layer 80 and sealed to the normal skin 24 surrounding the wound 25. If the cover 40 and the temperature sensitive layer 80 are an integrated unit, however, the unit is placed over the packing material or matrix 32a without a separate temperature sensitive layer 80. If the cover 40 is composed of a temperature sensitive material, it is placed over the packing material or matrix without an additional temperature sensitive layer 80. It should be noted, however, that the temperature sensitive material used in this embodiment of the invention is intended as a means to provide an approximate visual indication of the temperature in the area of the wound 25 beneath the cover 4, and may not accurately measure the actual temperature beneath the cover 40.

Figure 7:
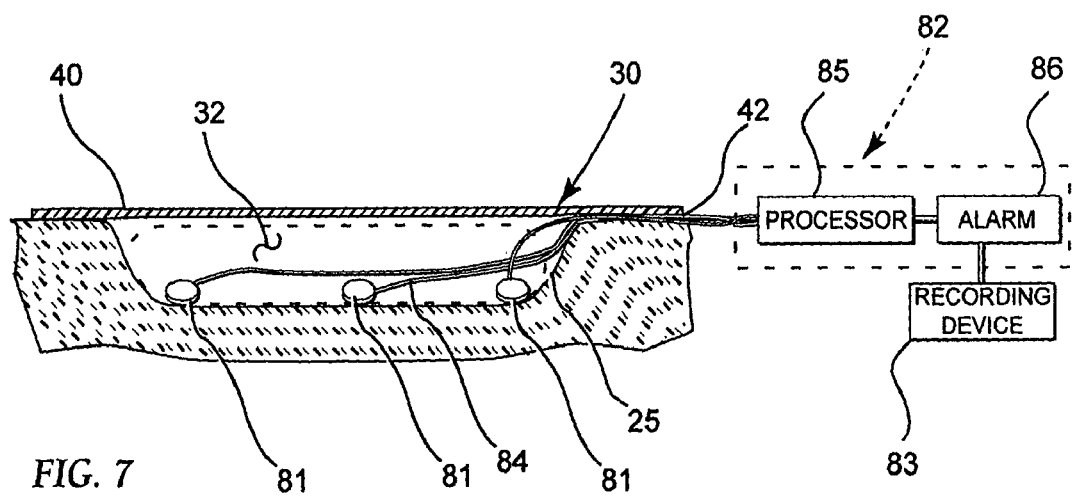
FIG. 7 is a schematic sectional elevational view of a reduced pressure appliance in accordance with another embodiment of the present invention, shown in partial section, in which the reduced pressure appliance includes a packing material positioned in the wound, and a flexible, fluid impermeable wound cover sealed over the wound, and a plurality of temperature sensors located at and surrounding the site of the wound, and in which an alarm system and a temperature display and recording device are connected to the temperature sensors.

In another embodiment of this second version of the invention, one or more temperature measuring devices 81 are placed within the area of the wound 25 and connected to an alarm system, generally designated as 82. The temperature measuring devices 81 may also be connected to a temperature display and recording device 83. An example of this embodiment is illustrated in FIG. 7, which shows temperature measuring devices 81 placed in the area of the wound 25. The temperature measuring devices 81 may be placed in any area of the wound 25 and the reduced pressure appliance 30. For example, the temperature measuring devices 81 may be placed adjacent to and in direct contact with the tissue in the area of the wound 25. Alternatively, the temperature measuring devices 81 may be embedded in any packing material or matrix 32 placed in the area of the wound 25, or in the area between such packing material or matrix 32 and the cover 40, or embedded within the cover 40, or adjacent to either surface of the cover 40.

The temperature measuring devices 81 are preferably capable of measuring temperatures in the range of temperatures expected in the area of the wound 25. More preferably, the temperature measuring devices 81 are capable of measuring temperatures in the range of 95 degrees Fahrenheit to 105 degrees Fahrenheit. The temperature measuring devices 81 may be any device that measures temperature in the desired range and produces a corresponding signal that may be interpreted by the alarm system 82 and temperature display and recording device 83. The temperature measuring devices 81 must, however, not be harmful to body tissue. The temperature measuring devices 81 are preferably thermocouples or optical sensors or detectors. The temperature measuring devices 81 are more preferably thermocouples that generate an electronic signal representing the temperature measured by the thermocouple.

The temperature measuring devices 81 are connected by leads 84 to an alarm system 82. The leads 84 may be in any form compatible with the temperature measuring devices 81 and the alarm system 82 and recording device 83. Preferably, the leads 84 are cables or wires constructed of an electrically conductive material, optical fiber, or other medium enabling data transmission that transfers the signals from the temperature measuring devices 81 to the alarm system 82 and the display and recording device 83. Leads 84 placed under the wound cover 40 feedthrough the seal 42 beneath the cover 40 in a manner similar to that for the tubing (as illustrated and discussed above in connection with FIG. 1) that maintains the fluid impermeable nature of the seal 42.

The alarm system 82 is comprised of a computer or other data processor 85 and an alarm device 86. The computer or data processor 85 receives the signals from the temperature measuring devices 81 and converts them to electronic or other signals that are recognized by the alarm device 86. The computer or data processor 85 is of a type that is commonly available in the relevant art. The alarm device 86 may produce any type of audible sound as an alarm, such as a ringing sound, buzzing, chirping or other common alarm noise. Alternatively, the alarm device 86 may include a digitally produced audible voice that presents predetermined messages corresponding to different temperature conditions in the area of the wound 25. The alarm device 86 preferably produces different levels of alarm depending upon the temperature measurements received from the temperature measuring devices 81. For example, as the temperature drops below or rises above successive preselected values of temperature, as measured by any temperature measuring device 81, the alarm device 86 may sound successive predetermined alarm pitches, sounds, messages or series of sounds. Similarly, as the temperature measured by multiple temperature measuring devices 81 successively falls below or rises above a preselected temperature, the alarm device 86 may sound successive predetermined alarm pitches, sounds, messages or series of sounds. The alarm system 82 may also be connected to the vacuum supply 50, so that upon production of a predetermined alarm by the alarm device 86, the vacuum pump controller 52 causes the pump 51 to cease operation.

The computer or data processor 85 may also be connected to a temperature display and recording device 83 that records the temperatures measured by one or more of the temperature measuring devices 81. The temperature recording device 83 may be any device designed to record or display data that is compatible with the signals produced by the computer or data processor 85. Such devices are preferably devices that record data on compact disks, floppy disks, magnetic tape, integrated circuits, or other similar media in digital form or "manual" devices that record or display data in a visually depicted form, such as a chart recorder or visual electronic display, such as an LCD or CRT monitor. The more preferred temperature display and recording device 83 is a device recording data on a compact disk used in conjunction with an LCD monitor.

It should be noted that in this embodiment of this version of the invention the cover 40 may be of any configuration, including the cover configuration illustrated in FIG. 3 and the other cover configurations specifically discussed above in connection with FIG. 3. In addition, it is not necessary that any packing material or matrix 32 be present in the area of the wound 25 beneath the cover 40 in this version of the invention. It is also not necessary that the temperature display and recording device 83 be included in every embodiment of this version of the invention. Nor is it necessary that the features included in this version of the invention be included as a part of any other version or embodiment of this invention.

In another version of the invention, the wound treatment apparatus 220 is portable and may be self-contained. In a first embodiment of this version of the invention, as illustrated in FIG. 8a, a miniature and portable vacuum source 250 is connected to a wound cover. The vacuum source 250 is preferably a miniature and portable vacuum pump. The vacuum source 250 may also be connected to a filter 253, which is connected to a collection system 270. The vacuum source 250 is used to provide suction to the reduced pressure appliance, generally designated as 230. It is portable in the sense that it is of a size small enough to be positioned directly on the surface of the wound cover 240. The vacuum source 250 is also lightweight to avoid placing too much pressure on any body part being treated by the apparatus 220 and to allow the apparatus 220 to be easily transported. The vacuum source 250 may be powered by electricity received through a cord plugged into a standard wall socket, or the vacuum source 250 may be powered by a battery, fuel cell, or other alternative means, such as solar or photo electric sells or a windmill or watermill operated generator. The vacuum source 250 may also be operated by other means, such as pneumatics or hydraulics, if such means are available.

The wound cover 240 may be of almost any size, shape, and configuration adapted to treat the wound. Thus, the wound cover 240 is not limited to the embodiment illustrated in FIG. 8*a*. As illustrated and discussed above in relation to FIG. 3, the cover may be comprised of a rigid, fluid impermeable, cone-shaped, bowl-shaped, or cup-shaped wound cover to protect the site of a wound 25 from impact or abrasion during treatment. Alternatively, the cover may be comprised of a flexible or rigid flat wound cover.

The vacuum source 250 may be attached to the cover 240 using any means that is compatible with the structure of the cover 240 and the vacuum source 250. For example, if the cover 240 is constructed of a flexible, fluid impermeable material, the vacuum source 250 may be attached to the cover 240 using an adhesive material, such as a glue or other liquid or sprayed adhesive, adhesive tape, and similar means that are currently known in the relevant art or which may hereafter be discovered. As another example, if the wound cover 240 is constructed of a rigid material, the vacuum source 250 may be attached to the cover 240 using a variety of fasteners and similar means, such as anchors, bolts, rivets, screws, nuts, latch and clasp, hook and loop fasteners (such as that commonly sold under the trade name VELCRO), ultrasonic welding, and similar structures that are currently known in the relevant art or which may hereafter be discovered. The vacuum source 250 may therefore be permanently attached to the cover 240, or the vacuum source 250 may be removably attached to the cover 240 allowing the vacuum source 250 to be reused after being used for a treatment even if the cover 240 is no longer usable after such treatment. The means of fastening the vacuum source 250 to the cover 240 must, however, be accomplished in a manner that allows the cover 240 to maintain the desired reduced pressure beneath the cover 240 while it is in use. Thus, gasket or sealant material may be used to seal any areas of perforation of the cover 240 where the fastener penetrates the surface of the cover 240.

The fluid collection system 270 in the embodiment illustrated in FIG. 8*a* includes a container 271 to collect the exudate and a shutoff mechanism 275, one embodiment of which is illustrated in FIG. 8*b*, to halt operation of the vacuum source 250 if the level of exudate in the container 271 exceeds a predetermined level. The container 271 is of the minimum size desired to collect and maintain the amount of exudate expected to be aspirated from the wound during the time of anticipated use of the portable wound treatment apparatus 220. Alternatively, a small container 271 may be used, in which the fluid is changed intermittently as necessary during the treatment period. The container 271 has two ports, a first port 272 for connecting the container 271 to the reduced pressure appliance 230 and a second port 273 for connecting the container 271 to the vacuum source 250. A filter 253 may also be connected intermediate the vacuum source 250 and the container 271. The shutoff mechanism may be comprised of any means that enables the vacuum system 250 to halt the supply of reduced pressure to the wound cover 240 at any time the volume of exudate from the wound exceeds a predetermined amount to prevent, thereby preventing such exudate from contaminating the vacuum source 250. Such means may include mechanical switches, electrical switches operably connected to the vacuum source 250, optical, thermal or weight sensors operably connected to the vacuum source 250, and any other means that are currently known in the relevant art or which may hereafter be discovered. Where the shutoff mechanism transfers electrical or other data signals to the vacuum source 250, the vacuum source 250 may contain a control mechanism to convert said signals to the form necessary to halt the production of reduced pressure by the vacuum source 250. Such means is preferably the float valve shutoff mechanism 275 illustrated in FIG. 8*b*, connected to the second port 273 of the container 271, which has the same features as the float valve illustrated in and discussed above in connection with FIG. 4*a*.

As illustrated in FIG. 8*a*, this embodiment of the invention may also include a filter 253 to prevent potentially pathogenic microbes or aerosols from contaminating the vacuum source 250. The filter 253 is generally comprised of a filter element encased in a fluid impermeable housing that has an inlet port 256 and an outlet port 257. The filter element is preferably a hydrophobic and micropore filter capable of filtering out pathogenic microbes or aerosols. The housing of the filter 253 may be constructed in a manner that enables the filter element to be changed if desired. The filter 253 need not, however, be used in every embodiment of this version of the invention.

In the embodiment illustrated in FIG. 8*a*, tubing 245 is used to connect the reduced pressure appliance 230 covering a wound 225 to the collection system 270 by means of the first port 272 located on the container 271. The features of this tubing 245 and reduced pressure appliance 230 are substantially the same as illustrated and discussed above in connection with FIG. 1 and FIG. 4*a*. In addition, in the embodiment of the invention illustrated in FIG. 8*a*, the second port 273 of the container 271 is connected to the inlet port 256 of the filter 253 by flexible vacuum tubing 254, such as that used to connect the collection system 270 to the reduced pressure appliance 230. This is not, however, the only means of connecting the collection system 270 to the filter 253. For example, the connection may be made by using a rigid, fluid impermeable structure, such as a short length of rigid polymer tube, permanently connecting the filter 253 and the collection system 270. The filter 253 may also be directly attached to the container 271 without the use of any tubing or other means, causing the container 271 and the filter 253 to be integrated as a single unit. In the embodiment of the invention illustrated in FIG. 8*a*, the outlet port 257 of the filter 253 is connected to the vacuum source 250 by flexible vacuum tubing 254*a*, such as that used to connect the collection system 270 to the reduced pressure appliance 230. This is not, however, the only means of connecting the collection system 270 to the filter 253. For example, the connection may be made by using a rigid, fluid impermeable structure, such as a short length of rigid polymer tube permanently connecting the filter 253 and the vacuum source 250. The filter 253 may also be directly attached to the vacuum source 250 without the use of any tubing or other means, causing the container 271 and the filter 253 to be integrated as a single unit. As illustrated in FIG. 8*a*, the vacuum source 250, the filter 253, and the container 271 may also be directly attached to one another to form a single integrated unit. Such attachment may be made by any of the means described above that may be used to attach the vacuum source 250 to the cover 240.

Use of the wound treatment apparatus can be illustrated by a prospective example involving a reduced pressure appliance 30 of the type discussed in connection with FIG. 1. After preparing the bed of the wound 25, one end of a length of vacuum tubing 45 is embedded in an absorbable matrix 32 that is trimmed to be the size and shape of the wound 25. The matrix 32 is saturated with saline and placed in the wound 25. As illustrated in FIG. 7, if temperature monitoring is desired, temperature measuring devices 81 are placed in the desired locations and connected to an alarm system 82, and if desired, a display and recording device 83. Alternatively, a temperature sensitive layer 80 is placed over the matrix, as illustrated in FIG. 6. A fluid impermeable or gas impermeable flexible adhesive sheet 40, such as IOBAN, is placed over the matrix 32 (and temperature measuring means, if utilized) and the wound 25 and sealed to the normal skin 24 surrounding the wound 25. The site of feedthrough of the vacuum tube 45 and any leads 84 from under the cover 40 is then sealed with a liquid or paste adhesive. Negative pressure is then applied to the reduced pressure appliance 30 by the vacuum system 50, through the intermediate fluid collection system 70.

Negative pressure appliances are useful for treating a variety of wounds. Treatment of a wound can be carried out by securing a negative pressure appliance to the treatment site as previously shown and described, and then maintaining a substantially continuous or cyclical reduced pressure within the appliance until the wound has reached a desired improved condition. A selected state of improved condition may include formation of granulation tissue sufficient for the attachment of a flap or graft, reduction of microbial infection in the wound, arrest or reversal of burn penetration, closure of the wound, integration of a flap or graft with the underlying wounded tissue, complete healing of the wound, or other stages of improvement or healing appropriate to a given type of wound or wound complex.

It may be preferable to change the appliance periodically during treatment, particularly when using appliances incorporating a packing material on or in the wound. The time between changing the appliance where an absorbable matrix is placed on or in the wound would ordinarily be a greater time interval that is generally dependent upon the nature of the wound. Where it is necessary to change the absorbable matrix during the treatment period, it may also be necessary to remove a portion of the matrix, but leave in place the portion of the matrix into which there has been significant tissue growth. In such cases, the portion of the matrix without significant tissue growth incorporated therein should be carefully removed by cutting or tearing away such portion from the remaining portion. New absorbable material can be placed in the area from which the prior material has been removed.

The wound treatment apparatus is preferably operated using a negative or reduced pressure ranging from 0.01 to 0.99 atmospheres, and more preferably practiced using a negative or reduced pressure ranging between 0.5 to 0.8 atmospheres. The time period for use of the wound treatment apparatus on a wound may preferably be at least 12 hours, but can be, for example, extended for one or more days. There is no upper limit beyond which use of the wound treatment apparatus is no longer beneficial; use of the wound treatment apparatus increases the rate of closure up to the time the wound actually closes. Satisfactory treatment of various types of wounds has been obtained via the use of reduced pressures equivalent to about 2 to 7 in. Hg below atmospheric pressure.

Supplying reduced pressure to the appliance in an intermittent or cyclic manner has also been demonstrated to be useful for treating wounds. Intermittent or cyclic supply of reduced pressure to an appliance may be achieved by manual or automatic control of the vacuum system 50. A cycle ratio, the ratio of "on" time to "off" time, in such an intermittent reduced pressure treatment may be as low as 1:10 or as high as 10:1. The preferred ratio is approximately 1:1 which is usually accomplished in alternating 5 minute intervals of reduced pressure supply and non-supply.

A suitable vacuum system 50 includes any suction pump capable of providing at least 0.1 pounds of suction to the wound, and preferably up to three pounds suction, and most preferably up to fourteen (14) pounds suction. The pump can be any ordinary suction pump suitable for medical purposes that is capable of providing the necessary suction. The dimension of the tubing interconnecting the pump and the reduced pressure appliance is controlled by the pump's ability to provide the suction level needed for operation. A ¼ inch diameter tube may be suitable.

In treating damaged tissue, use of the invention usually comprises the steps of applying negative pressure to a wound for a selected time and at a selected magnitude sufficient to reduce bacterial density in the wound. Open wounds are almost always contaminated with harmful bacteria. The application of negative pressure to a wound appears to reduce the bacterial density of the wound. It is believed that this effect is due to either the bacteria's incompatibility with a negative pressure environment or the increased blood flow to the wound area, as blood brings with it cells and enzymes to destroy the bacteria.

Burns may generally be treated using a method that comprises the steps of applying negative pressure to the burn over an area with predetermined reduced pressure and for a time sufficient to inhibit formation of a full thickness burn. A partial thickness burn, one which has a surface layer of dead tissue and an underlying zone of stasis, is often sufficiently infected so that it will transform within 24-48 hours into a full thickness burn, one in which all epidermal structures are destroyed. The application of negative pressure to the wound prevents the infection from becoming sufficiently severe to cause destruction of the underlying epidermal structures. The magnitude, pattern, and duration of pressure application can vary with the individual wound.

What is claimed is:

1. An apparatus for the treatment of a wound, comprising:
    a flexible wound cover;
    a container in direct contact with and in fluid communication with the wound cover, the container being configured to retain fluid from the wound;
    a vacuum source in fluid communication with the container; and
    a hydrophobic filter interposed between the container and the vacuum source.

2. The apparatus of claim 1, wherein at least the wound cover, the container and the filter are integrated into a single unit.

3. The apparatus of claim 2, wherein the vacuum source is removably attached to the wound cover.

4. The apparatus of claim 1, wherein the apparatus is self-contained and portable.

5. The apparatus of claim 1, further comprising a battery power source.

6. The apparatus of claim 1, wherein the filter is integrated into the container.

7. The apparatus of claim 1, further comprising a vacuum source shutoff mechanism responsive to the fluid level in the container.

8. The apparatus of claim 7, wherein the vacuum source further comprises a control mechanism responsive to a signal sent from the shutoff mechanism.

9. The apparatus of claim 1, further comprising a flexible padding under the cover.

10. The apparatus of claim 1, further comprising an adhesive material disposed on the cover so as to create a substantially fluid-tight seal to the skin surrounding the wound.

11. The apparatus of claim 1, further comprising a porous screen disposed underneath the cover, the porous screen being constructed so as to permit the passage of fluids and gasses.

12. The apparatus of claim 1, further comprising a packing material underneath the cover.

13. The apparatus of claim 1, further comprising an absorbable material configured to be placed between the wound cover and the wound.

14. The apparatus of claim 1, wherein the wound cover is fluid-impermeable.

15. The apparatus of claim 1, wherein the cover further comprises a port in fluidic connection with the vacuum source.

16. The apparatus of claim 1, wherein the vacuum source is connected to the container via tubing.

17. The apparatus of claim 1, further comprising at least one monitor on or under the wound cover configured to monitor wound treatment.

18. The apparatus of claim 17, wherein the monitor is configured to monitor pressure beneath the wound cover.

19. The apparatus of claim 17, wherein the monitor is configured to monitor temperature in the area of the wound.

20. The apparatus of claim 17, comprising a plurality of monitors on the wound cover configured to provide a visual indication of the wound treatment.

21. The apparatus of claim 17, wherein the wound cover comprises a transparent or semi-transparent material to allow visualization through the wound cover.

22. The apparatus of claim 1, further comprising a shutoff mechanism configured to halt the supply of negative pressure to the wound cover.

23. The apparatus of claim 22, wherein the shutoff mechanism comprises an electrical switch operably connected to a vacuum system controller connected to the vacuum source.

24. The apparatus of claim 22, wherein the shutoff mechanism comprises an optical sensor operably connected to a vacuum system controller connected to the vacuum source.

25. An apparatus for the treatment of a wound, comprising:
a wound cover;
a fluid collector integrated with the wound cover and configured to be positioned with the wound cover over the wound, the fluid collector configured to retain fluid from the wound, wherein the fluid collector is in direct contact with the wound cover;
a vacuum source configured to provide suction to the wound beneath the wound cover; and
a filter intermediate the fluid collector and the vacuum source.

26. The apparatus of claim 25, wherein the wound cover comprises a flexible flat wound cover.

27. The apparatus of claim 25, wherein the wound cover comprises a rigid, fluid impermeable material.

28. The apparatus of claim 25, wherein the wound cover is cone-shaped, bowl-shaped or cup-shaped.

29. The apparatus of claim 25, wherein the fluid collector comprises a container attached to the wound cover.

30. The apparatus of claim 25, wherein the vacuum source comprises a portable vacuum pump.

31. The apparatus of claim 25, wherein the filter is a hydrophobic or micropore filter.

32. The apparatus of claim 25, wherein the wound cover, vacuum source, filter and fluid collector are integrated as a single unit directly attached to each other or the wound cover.

33. The apparatus of claim 25, further comprising an absorbable material configured to be positioned between the wound cover and the wound.

34. The apparatus of claim 25, further comprising at least one tube connected with the vacuum source configured to provide suction from the vacuum source to the wound.

35. The apparatus of claim 25, further comprising at least one monitor on or under the wound cover configured to monitor wound treatment.

36. The apparatus of claim 35, wherein the monitor is configured to monitor pressure beneath the wound cover.

37. The apparatus of claim 25, further comprising a shutoff mechanism configured to halt the supply of suction to the wound cover.

38. The apparatus of claim 37, wherein the shutoff mechanism comprises an electrical switch operably connected to a vacuum system controller connected to the vacuum source.

39. The apparatus of claim 37, wherein the shutoff mechanism comprises an optical sensor operably connected to a vacuum system controller connected to the vacuum source.

40. The apparatus of claim 25, further comprising a sealing ring secured to the wound cover.

41. The apparatus of claim 25, wherein the wound cover comprises a flexible polymer sheet.

42. An apparatus for the treatment of a wound, comprising:
a wound cover configured to be positioned over a wound; and
a vacuum source adjacent the wound cover configured to apply negative pressure to the wound, wherein the vacuum source and the wound cover form a single unit and the vacuum source is configured to be positioned with the wound cover over a patient,
wherein the wound cover defines a periphery and the vacuum source is located within the periphery of the wound cover.

43. The apparatus of claim 42, further comprising a fluid collector attached to the wound cover.

44. The apparatus of claim 43, further comprising a filter configured to prevent material from contaminating the vacuum source.

45. The apparatus of claim 44, wherein the vacuum source, filter and fluid collector form a single integrated unit configured to be positioned with the wound cover over the wound.

46. The apparatus of claim 42, wherein the vacuum source is in direct contact with the wound cover.

47. The apparatus of claim 46, wherein the vacuum source is attached to an outer surface of the wound cover.

48. The apparatus of claim 43, wherein the fluid collector is in direct contact with the wound cover.

49. The apparatus of claim 42, further comprising at least one monitor on or under the wound cover configured to monitor wound treatment.

50. The apparatus of claim 49, wherein the monitor is configured to monitor pressure beneath the wound cover.

51. The apparatus of claim 49, wherein the monitor is configured to monitor temperature in the area of the wound.

52. The apparatus of claim 49, comprising a plurality of monitors on the wound cover configured to provide a visual indication of the wound treatment.

53. The apparatus of claim 42, further comprising a shutoff mechanism configured to halt the supply of negative pressure to the wound cover.

54. The apparatus of claim 53, wherein the shutoff mechanism comprises an electrical switch operably connected to a vacuum system controller connected to the vacuum source.

55. The apparatus of claim 53, wherein the shutoff mechanism comprises an optical sensor operably connected to a vacuum system controller connected to the vacuum source.

56. The apparatus of claim 42, wherein the vacuum source is battery-powered.

57. The apparatus of claim 42, wherein the wound cover comprises a flexible sheet.

58. The apparatus of claim 42, wherein the wound cover comprises a rigid, fluid-impermeable material.

59. The apparatus of claim 42, further comprising a sealing ring secured to the wound cover.

60. The apparatus of claim 42, wherein the wound cover comprises a flexible sheet.

61. A method of treating a wound, comprising:
positioning a wound treatment apparatus comprising a wound cover and a fluid collector integrated with the wound cover over a wound;
applying negative pressure to the wound with a vacuum source to draw wound exudate into the fluid collector, wherein the fluid collector is in direct contact with the wound cover as negative pressure is being applied; and
retaining wound exudate within the fluid collector as the negative pressure is being applied with the fluid collector positioned over the wound.

62. The method of claim 61, further comprising sealing the wound cover to skin surrounding the wound.

63. The method of claim 61, further comprising powering the vacuum source with a battery.

64. The method of claim 61, further comprising shutting off the vacuum source if the fluid level in the fluid collector exceeds a predetermined amount.

65. The method of claim 61, wherein the negative pressure is applied to the wound through a filter between the fluid collector and the vacuum source.

66. The method of claim 61, wherein the wound exudate is drawn into a container attached to the wound cover.

67. The method of claim 61, wherein the fluid collector is positioned above the wound cover.

68. The method of claim 61, wherein negative pressure is applied to the wound through at least one tube between the vacuum source and the wound cover.

69. The method of claim 61, further comprising monitoring wound treatment with at least one monitor on the wound treatment apparatus.

70. The method of claim 61, wherein monitoring comprises monitoring the pressure beneath the wound cover.

71. The method of claim 61, further comprising ceasing the application of negative pressure in response to a shutoff mechanism responsive to the volume of exudate in the fluid collector exceeding a predetermined amount.

72. The method of claim 71, wherein the shutoff mechanism is an electrical switch operably connected to a vacuum system controller connected to the vacuum source.

73. The method of claim 71, wherein the shutoff mechanism is an optical sensor.

74. The method of claim 61, wherein the negative pressure is applied cyclically.

75. The method of claim 62, wherein sealing the wound cover comprises applying a sealing ring secured to the wound cover to a region of skin surrounding the wound.

76. An apparatus for the treatment of a wound, comprising:
a wound cover;
a fluid collector integrated with the wound cover and configured to be positioned with the wound cover over the wound, the fluid collector configured to retain fluid from the wound;
a vacuum source configured to provide suction to the wound beneath the wound cover, wherein the vacuum source comprises a portable vacuum pump, and wherein the vacuum pump is directly attached to the cover; and
a filter intermediate the fluid collector and the vacuum source.

77. A method of treating a wound, comprising:
positioning a wound treatment apparatus comprising a wound cover and a fluid collector integrated with the wound cover over a wound;
applying negative pressure to the wound with a vacuum source to draw wound exudate into the fluid collector, wherein the vacuum source is directly attached to the wound cover; and
retaining wound exudate within the fluid collector as the negative pressure is being applied with the fluid collector positioned over the wound.

78. A method of treating a wound, comprising:
positioning a wound treatment apparatus comprising a wound cover and a fluid collector integrated with the wound cover over a wound;
applying negative pressure to the wound with a vacuum source to draw wound exudate into the fluid collector;
retaining wound exudate within the fluid collector as the negative pressure is being applied with the fluid collector positioned over the wound; and
monitoring wound treatment with at least one monitor on the wound treatment apparatus, wherein monitoring comprises monitoring the temperature in the area of the wound.

79. A method of treating a wound, comprising:
positioning a wound treatment apparatus comprising a wound cover and a fluid collector integrated with the wound cover over a wound;
applying negative pressure to the wound with a vacuum source to draw wound exudate into the fluid collector;
retaining wound exudate within the fluid collector as the negative pressure is being applied with the fluid collector positioned over the wound; and
monitoring wound treatment with at least one monitor on the wound treatment apparatus, wherein monitoring the wound treatment is performed visually with a plurality of monitors on the wound cover.

80. An apparatus for the treatment of a wound, comprising:
a wound cover;
a fluid collector integrated with the wound cover and configured to be positioned with the wound cover over the wound, the fluid collector configured to retain fluid from the wound;
a vacuum source configured to provide suction to the wound beneath the wound cover;
a filter intermediate the fluid collector and the vacuum source; and
at least one monitor on or under the wound cover configured to monitor wound treatment, wherein the monitor is configured to monitor temperature in the area of the wound.

81. An apparatus for the treatment of a wound, comprising:
a wound cover;
a fluid collector integrated with the wound cover and configured to be positioned with the wound cover over the wound, the fluid collector configured to retain fluid from the wound;
a vacuum source configured to provide suction to the wound beneath the wound cover;
a filter intermediate the fluid collector and the vacuum source; and a plurality of monitors on the wound cover configured to provide a visual indication of the wound treatment.

82. An apparatus for the treatment of a wound, comprising:
a wound cover;
a fluid collector integrated with the wound cover and configured to be positioned with the wound cover over the wound, the fluid collector configured to retain fluid from the wound;
a vacuum source configured to provide suction to the wound beneath the wound cover;
a filter intermediate the fluid collector and the vacuum source; and
at least one monitor on or under the wound cover configured to monitor wound treatment, wherein the wound cover comprises a transparent or semi-transparent material to allow visualization through the wound cover.

83. An apparatus for the treatment of a wound, comprising:
a wound cover;
a fluid collector integrated with the wound cover and configured to be positioned with the wound cover over the wound, the fluid collector configured to retain fluid from the wound;
a vacuum source configured to provide suction to the wound beneath the wound cover; and
a filter intermediate the fluid collector and the vacuum source;
wherein the wound cover defines a periphery and the fluid collector is located within the periphery of the wound cover.

84. The apparatus of claim 83, wherein the wound cover comprises a flexible polymer sheet.

85. The apparatus of claim 84, further comprising an adhesive on an underside of the wound cover.

86. The apparatus of claim 85, further comprising an adhesive strip configured to be positioned over at least a portion of the cover.

87. The apparatus of claim 83, further comprising a sealing ring secured to the wound cover.

88. The apparatus of claim 83, wherein the vacuum source comprises a portable, battery powered vacuum pump configured to be connected to the wound cover by at least one tube.

89. The apparatus of claim 83, wherein the filter is a hydrophobic or micropore filter.

90. The apparatus of claim 83, wherein the wound cover, filter and fluid collector are integrated as a single unit directly attached to each other or the wound cover.

91. The apparatus of claim 83, further comprising at least one monitor on or under the wound cover configured to monitor wound treatment.

92. The apparatus of claim 83, further comprising a plurality of monitors on the wound cover configured to provide a visual indication of the wound treatment.

93. The apparatus of claim 83, wherein the wound cover comprises a transparent or semi-transparent material to allow visualization through the wound cover.

* * * * *

UNITED STATES PATENT AND TRADEMARK OFFICE
CERTIFICATE OF CORRECTION

PATENT NO.       : 8,118,794 B2
APPLICATION NO.  : 12/938291
DATED            : February 21, 2012
INVENTOR(S)      : Richard Scott Weston Page 1 of 1

It is certified that error appears in the above-identified patent and that said Letters Patent is hereby corrected as shown below:

Title page at (Item 56) Page 3, Column 1, Line 69, Under Other Publications, change "Problemwuden"" to --Problemwunden"--.

Title page at (Item 56) Page 3, Column 2, Line 29, Under Other Publications, change "V. Schmeiden," to --V. Schmieden,--.

Title page at (Item 56) Page 3, Column 2, Line 63, Under Other Publications, change "salmoncida:" to --salmonicida:--.

At Column 8, Line 21, Change "collogens" to --collagens--.

At Column 9, Line 16, Change "of" to --or--.

At Column 17, Line 6, Change "sells" to --cells--.

At Column 23, Line 46, In Claim 70, change "61," to --69,--.

Signed and Sealed this
Third Day of July, 2012

David J. Kappos
*Director of the United States Patent and Trademark Office*